United States Patent [19]

Haseloff et al.

[11] Patent Number: 5,494,814
[45] Date of Patent: * Feb. 27, 1996

[54] RIBOZYMES

[75] Inventors: James P. Haseloff, O'Connor; Wayne L. Gerlach, Hughes; Philip A. Jennings, West Chatswood; Fiona H. Cameron, Forestville, all of Australia

[73] Assignee: Gene Shears Pty. Limited, Canberra City, Australia

[ * ] Notice: The portion of the term of this patent subsequent to Oct. 19, 2010, has been disclaimed.

[21] Appl. No.: 967,693

[22] Filed: Oct. 27, 1992

Related U.S. Application Data

[63] Continuation of Ser. No. 926,148, Aug. 5, 1992, Pat. No. 5,254,678, which is a continuation of Ser. No. 536,625, Aug. 14, 1990, abandoned.

[30] Foreign Application Priority Data

Dec. 15, 1987 [AU] Australia ............................. PI5911/87
Aug. 19, 1988 [AU] Australia ............................. PI9950/88
Sep. 9, 1988 [AU] Australia ............................. PJ0353/88
Nov. 4, 1988 [AU] Australia ............................. PJ1304/88
Nov. 7, 1988 [AU] Australia ............................. PJ1333/88

[51] Int. Cl.$^6$ .............................. C12N 5/10; C12N 9/22; C12N 15/54; C12Q 1/68
[52] U.S. Cl. ........................ 435/172.3; 435/6; 435/91.31; 435/199; 435/252.3; 435/240.1; 435/240.2; 435/320.1; 536/23.1; 536/23.2; 536/24.5
[58] Field of Search ........................ 435/6, 91.31, 172.3, 435/320.1, 240.1, 280.2, 240.4, 252.3, 254.11, 199; 536/23.1, 24.5, 23.2; 514/44

[56] References Cited

U.S. PATENT DOCUMENTS 4,987,071  1/1991  Cech et al. ........................... 435/91.31

OTHER PUBLICATIONS

Boehm, S., (1987), "Similarities between a predicted secondary structure for the M$_1$ RNA ribozyme and the tRNA binding center of the 16S rRNA from *E.coli*" FEBS Letters, 220: 283–287.
Bruening, G. (1989) "Compilation of Self–Cleaving Sequences from Plant Virus Satellite RNAs and Other Sources", Methods in Enzymology 180: 546–558.
Cech, T. R. (1987) "The Chemistry of Self–Splicing RNA Enzymes", Science, 236: 1532–1539.
Chuat, J. et al., (1989) "Can Ribozymes Be Used To Regulate Procaryote Gene Expression?", Biochemical and Biophysical Research Communications, 162: 1025–1029.
Cotten, M. et al., (1989) "Ribozyme Mediated Destruction of RNA in vivo" The EMBO Journal, 8: 3861–3866.
Eckner, R. et al., (1991) "Mature mRNA 3' End Formation Simulates RNA Export from the Nucleus" The EMBO Journal 10: 3513–3522.
Forster, A. C. et al., (1988) "Self–cleaving Viroid and Newt RNAs May Only Be Active As Dimers" Nature 334: 265–267.

Forster, A. C. and Symons R. H., (1987) "Self–cleavage of Plus and Minus RNAs of a Virusoid and a Structural Model for Active Sites" Cell 49: 211–220.
Haseloff, J. and W. L. Gerlach (1988) "Simple RNA enzyme with new and highly specific endoribonuclease activities" Nature, 334: 585–591.
Huillier, A. et al., Ribozyme mediated suppression of lactalbumin Expressed in C1271 Cells by T7/Vaccinia Virus (Abstract from conference proceedings).
Hutchins, C. J. et al., (1986) "Self–cleavage of plus and minus RNA transcripts of avocdao sunblotch virus" Nucleic Acids Research, 14: 3627–3635.
Kikuchi, Y. et al., (1991) "Site–specific cleavage of natural mRNA sequences by newly designed hairpin catalytic RNAs" Nucleic Acids Research, 19: 6751–6755.
Koizumi et al., (1988) "Construction of a series of several self–cleaving RNA duplexes using synthetic 21–mrs" FEBS Letters, 228, No. 2, 228–230.
Koizumi et al., (1989) "Design of RNA enzymes distinguishing a single base mutation in RNA" Nucleic Acids Research 17: 7059–7071.
Lamb, J. W. & Hay, R. T. (1990) "Ribozymes that cleave potato leafroll virus RNA within the coat protein and polymerase genes", J. Gen. Virol. 71: 2257–2264.
Miller, W. A. et al., (1991) "A Satellite RNA of Barley Yellow Dwarf Virus Contains a Novel Hammerhead Structure in the Self–cleavage Domain" Virology, 183: 711–720.
Ruffner, D. E. et al., (1989) "Studies on the hammerhead RNA self–cleaving domain" Gene 82: 31–41.
Ruffner, D. E. et al., (1990) "Sequence Requirements of the Hammerhead RNA Self–cleaving Reaction" Biochemistry 29: 10695–10702.
Sarver, N. et al., (1990) "Ribozymes as Potential Anti–HIV–1 Therapeutic Agents" Science, 247: 1222–1224.
Saxena, S. et al., (1990) "Ribozymes Correctly Cleave a Model Substrate and Endogenous RNA in vivo" J. Biol. Chem. 265: 17106–17109.
Scanlon, K. et al., (1991) "Ribozyme–mediated cleavage of c–fos RNA reduces gene expression of DNA synthesis enzymes and metallothionein" Proc. Natl. Acad. Sci. USA, 88:10591–10595.
Sheldon, C. C. & Symons, R. H. (1989) "RNA stem stability in the formation of a self–cleaving hammerhead structure" Nucleic Acids Research, 17: 5665–5678.
Sheldon, C. C. & Symons R. H., (1989) "Mutagenesis Analysis of a self–cleaving RNA" Nucleic Acids Research, 17: 5679–5686.

(List continued on next page.)

*Primary Examiner*—Jacqueline M. Stone
*Assistant Examiner*—J. LeGuyader
*Attorney, Agent, or Firm*—John P. White

[57] ABSTRACT

Compounds having highly specific endoribonuclease activity are described. The compounds of this invention, also known as ribozymes, comprise ribonucleotides having two hybridizing regions with predetermined sequences capable of hybridizing with a target RNA, a region of defined sequence and a base paired stem region.

6 Claims, 24 Drawing Sheets

OTHER PUBLICATIONS

Symons, R. H. (1989) "Self–cleavage of RNA in the replication of small pathogens of plants and animals" Tibs 14: 445–450.

Tabler, M. & Tsagris, M., (1991) "Catalytic antisense RNAs produced by incorporating ribozymes cassettes into cDNA" Gene 108: 175–183.

Zaug, A. J. & Cech, T. R. (1986) "The Tetrahymena ribozyme acts like an RNA restriction endonuclease" Science, 231: 473–474.

Zaug, A. J. et al., (1986) "The Tetrahymena ribozyme acts like an RNA restriction endonuclease" Nature, 324: 429–433.

Forster, A. C., et al. (1987) Cell 50:9–16.

McClain et al., (1987) Science 238:537–530.

Sampson, et al., (1987) Cold Spring Harbor Sym. Quant. Biol. 52:267–275.

Uhlenbeck, et al., (1987) Nature 328:596–600.

Motamedi et al. PNAS 81:3959–63 (1984) Provided as Medline Abstract Acc #84248038.

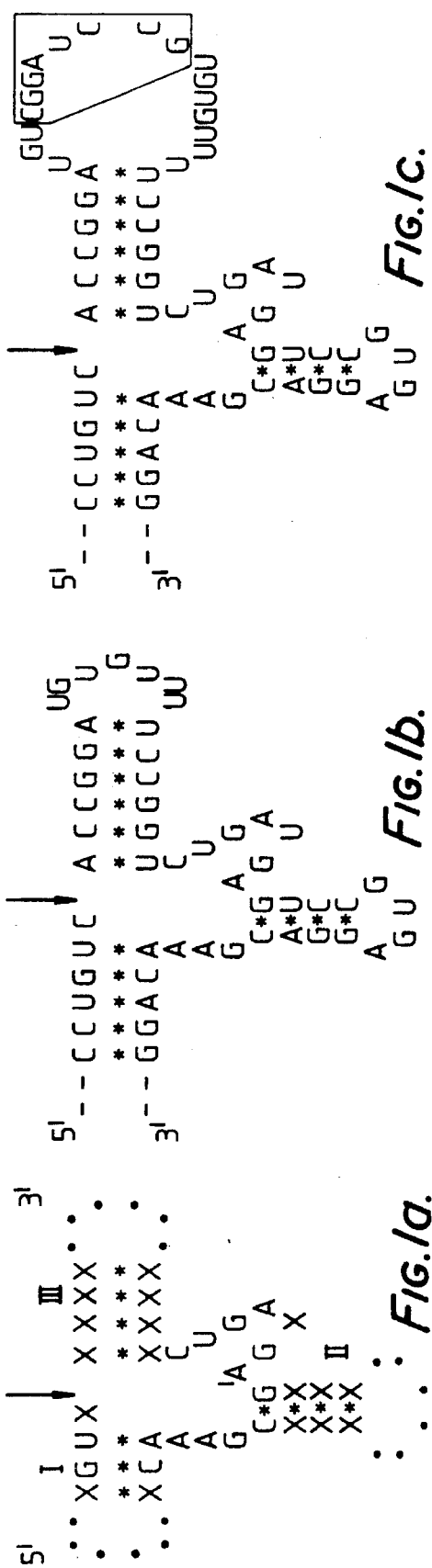

FIG. 8c

```
#139
    Ile Glu Asn Met Phe Phe Val   ↓Ser Ala Asn Pro Trp Val Ser
5' AUUGAGAAUAUGUUUUCGUC    UCAGCCAAUCCCUGGGUGAGU 3'
   ************  ****************
   AUACAAAAGCA    AGUCGGUUAGGGA
  3'          A  G                5'
              A  U
              G  A           2x12
              C*G
              A*U
              G*C
              G*C
              A  G
               GA
```

```
RIBOZYME CEV9x(+)   5' GAAGUCCUUCAG 3'
RIBOZYME CEV9x(-)   5' AGGGUCAGGUGA 3'
RIBOZYME CEV25x(+)  5' GAAGUCGAGGUC 3'
```

Fig. 11.

```
5' UCCCCGGGAAACCUGGAGGAAGUC         GAGGUCGGGGACAGCUG 3'
   * * * * * * * * * * * * *         * * * * * * * * * * * * * * * * *
3' AGGGGCCCUUUGGACCUCGUUCA          CUCCAGCCCUGUCGAC 5'
                         A    G
                          G  G
                           GGA U
                           * * *
                           CCU G
                          A    U
                         G      U
                          U U U G
```

Fig.12a.

CLEAVAGE PRODUCT

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

N N C U G A N G A G   N       1 1

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
  ( A ) NAME/KEY: misc_feature
  ( B ) LOCATION: 15
  ( D ) OTHER INFORMATION: /note="N represents a bond, a base
    pair, a ribonucleotide, or an
    oligonucleotide containing at least 2
    ribonucleotides"

( x i ) SEQUENCE DESCRIPTION: SEQ ID NO:2:

NNCUGANGAG NNNNNNNNC GAAAN     25

( 2 ) INFORMATION FOR SEQ ID NO:3:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:3:

His His Ala Val Cys Asp Gly
     5

( 2 ) INFORMATION FOR SEQ ID NO:4:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: RNA (genomic)

( x i ) SEQUENCE DESCRIPTION: SEQ ID NO:4:

CAUCAUGCCG UCUGUGAUGG C     21

( 2 ) INFORMATION FOR SEQ ID NO:5:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: RNA (genomic)

( x i ) SEQUENCE DESCRIPTION: SEQ ID NO:5:

NNNNCUGANG AGNNN     15

( 2 ) INFORMATION FOR SEQ ID NO:6:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA (genomic)

( x i ) SEQUENCE DESCRIPTION: SEQ ID NO:6:

NNNCGAAACN     10

( 2 ) INFORMATION FOR SEQ ID NO:7:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( i i ) MOLECULE TYPE: RNA (genomic)

( x i ) SEQUENCE DESCRIPTION: SEQ ID NO:7:

CCUGUCACCG GAUGUGUUUU CCGGUCUGAU GAGUCCGUGA GGACGAAACA GG    52

( 2 ) INFORMATION FOR SEQ ID NO:8:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:8:

CCUGUCACCG GAUGUCGGAU CCGUGUGUUU UCCGGUCUGA UGAGUCCGUG AGGACGAAAC    60

AGG    63

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

CCUGUCACCG GAUGUCG    17

( 2 ) INFORMATION FOR SEQ ID NO:10:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

GAUCCGUGUG UUUUCCGGUC UGAUGAGUCC GUGAGGACGA AACAGG    46

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:11:

NNNNNNNNN NNNGUCNNNN NNNNNNNNN    30

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:12:

NNNNNNNCU GAUGAGUCCG UGAGGACGAA ACNNNNNN 38

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ala Phe Gln Ser Val Ala Gln
              5

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:14:

GCAUUUCAGU CAGUUGCUCA A 21

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:15:

GAGCAACUCU GAUGAGUCCG UGAGGACGAA ACUGAAAU 38

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Phe Phe Val Ser Ala Asn
            5

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:17:

UGUUUUUCGU CUCAGCCAAU C 21

( 2 ) INFORMATION FOR SEQ ID NO:18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:18:

UUGGCUGACU GAUGAGUCCG AGAGGACGAA ACGAAAAA　　　　　　　　　　　　　　　38

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Phe His Val Gly Arg Met
                5

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:20:

GCUUCCAUGU CGGCAGAAUG C　　　　　　　　　　　　　　　　　　　　　　　　21

( 2 ) INFORMATION FOR SEQ ID NO:21:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:21:

AUUCUGCCCU GAUGAGUCCG UGAGGACGAA ACAUGGAA　　　　　　　　　　　　　　　38

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Ile Glu Asn Met Phe Phe Val Ser Ala Asn Pro Trp Val Ser
                5                    10

( 2 ) INFORMATION FOR SEQ ID NO:23:

( i ) SEQUENCE CHARACTERISTICS:
        ( A ) LENGTH: 42 base pairs
        ( B ) TYPE: nucleic acid ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:23:

AUUGAGAAUA UGUUUUUCGU CUCAGCCAAU CCCUGGGUGA GU                    4 2

( 2 ) INFORMATION FOR SEQ ID NO:24:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:24:

CUGACUGAUG AGUCCGAGAG GACGAAACGA                                   3 0

( 2 ) INFORMATION FOR SEQ ID NO:25:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:25:

UUGGCUGACU GAUGAGUCCG AGAGGACGAA ACGAAAAA                          3 8

( 2 ) INFORMATION FOR SEQ ID NO:26:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:26:

AGGGAUUGGC UGACUGAUGA GUCCGAGAGG ACGAAACGAA AAACAUA                4 7

( 2 ) INFORMATION FOR SEQ ID NO:27:

( i ) SEQUENCE CHARACTERISTICS:
            ( A ) LENGTH: 67 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:27:

NNNNNNCUG ANGAGNNNNN NNNNCGAAN NNNNNNNCUG ANGAGNNNNN NNNNCGAAA    6 0

CNNNNNN                                                            6 7

( 2 ) INFORMATION FOR SEQ ID NO:28:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:28:

NNNNNNNCU GANGAGNNNN NNNNNNCGAA ACNNNNNN  38

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:29:

AAGACCGUAA AGAAAAA  17

( 2 ) INFORMATION FOR SEQ ID NO:30:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:30:

UUUUUCUUCU GAUGAGUCCG UGAGGACGAA ACGGUCUU  38

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:31:

GAUAGUGUUC ACCCUUG  17

( 2 ) INFORMATION FOR SEQ ID NO:32:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:32:

CAAGGGUGCU GAUGAGUCCG UGAGGACGAA ACACUAUC  38

( 2 ) INFORMATION FOR SEQ ID NO:33:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:33:

GAAGUCCUUC AG  12

(2) INFORMATION FOR SEQ ID NO:34:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:34:

AGGGUCAGGU GA                                                                   12

(2) INFORMATION FOR SEQ ID NO:35:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:35:

GAAGUCGAGG UC                                                                 12

(2) INFORMATION FOR SEQ ID NO:36:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:36:

UCCCCGGGGA AACCUGGAGG AAGUCGAGGU CGGGGACAGC UG                 42

(2) INFORMATION FOR SEQ ID NO:37:

(i) SEQUENCE CHARACTERISTICS:
           (A) LENGTH: 63 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:37:

CAGCUGUCCC CGACCUCCUG AUGAGUCCGU GAGGACGAAA CUUGCUCCAG GUUUCCCCGG     60

GGA                                                                                        63

(2) INFORMATION FOR SEQ ID NO:38:

(i) SEQUENCE CHARACTERISTICS:
           (A) LENGTH: 10 amino acids
           (B) TYPE: amino acid
           (D) TOPOLOGY: linear (ii) MOLECULE TYPE: peptide (xi) SEQUENCE DESCRIPTION: SEQ ID NO:38:

Asn Met Phe Phe Val Ser Ala Asn Pro Trp
                 5                        10

(2) INFORMATION FOR SEQ ID NO:39:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:39:

AAUAUGUUUU UCGUCUCAGC CAAUCCCUGG        30

( 2 ) INFORMATION FOR SEQ ID NO:40:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:40:

AGGGAUUGGC UGACUGAUGA GUCCGAGAGG ACGAAACGAA AAACAUA        47

( 2 ) INFORMATION FOR SEQ ID NO:41:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:41:

AGGGAUUGGC UGACUGACGA GUCCCUAAAG GACGAAACGA AAAACAUA        48

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:42:

CCUGCAGGGU CAGGUGAGCA G        21

( 2 ) INFORMATION FOR SEQ ID NO:43:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:43:

CUGCUCACCU CUGAUGAGUC CGATATCCGG ACGAAACCCU GCAGG        45

( 2 ) INFORMATION FOR SEQ ID NO:44:

( i ) SEQUENCE CHARACTERISTICS:
        ( A ) LENGTH: 55 base pairs
        ( B ) TYPE: nucleic acid
        ( C ) STRANDEDNESS: single (D) TOPOLOGY: linear (i i) MOLECULE TYPE: RNA (genomic)

(x i) SEQUENCE DESCRIPTION: SEQ ID NO:44:

AGGGAUUGGC UGACUGAUGA GUCCGUCCGA GAGGACGGAC GAAACGAAAA ACAUA    55

RIBOZYMES

This application is a continuation of U.S. Ser. No. 926,148, filed Aug. 5, 1992, now U.S. Pat. No. 5,254,678 which is a continuation of U.S. Ser. No. 536,625, filed Aug. 14, 1990, now abandoned.

The present invention relates to a class of synthetic RNA molecules and derivatives thereof, hereinafter referred to as ribozymes, which possess highly specific endoribonuclease activity.

A number of naturally occurring RNA molecules such as avocardo sunblotch viroid (ASBV), the satellite RNAs of tobacco ringspot virus (sTobRV) and lucerne transient streak virus (sLTSV), undergo self-catalysed cleavage. Such cleavage appears to be an essential and unique part of the life cycle of these and other RNAs.

Self-catalysed RNA cleavage reactions share a common requirement for divalent metal ions and neutral or higher pH, and result in the production of RNA with termini possessing 5' hydroxyl and 2', 3' cyclic phosphate groups (Prody et al., Science 231: 1577–1580 (1986) and Buzayan et al., Virology 151: 186–199 (1986)). The cleavage reactions are catalysed by the RNAs themselves, presumably as a result of conformation bringing reactive groups into close proximity. The sites of self-catalysed cleavage in naturally occurring RNAs are located within highly conserved regions of RNA secondary structure (Buzayan et al., Proc. Natl. Acad. Sci. U.S.A. 83: 8859–8862 (1986) and Forster, A.C. and Symons, R. H. Cell 50: 9–16 (1987)).

Experiments we have carried out on the satellite RNAs of tobacco ringspot virus (sTobRV) have led to the design of novel endoribonucleases (hereinafter referred to as "ribozymes"), that is, enzymes comprised of RNA which catalyse specific cleavage of RNA target molecules.

The term ribozyme as used in the specification refers to molecules comprised wholly of RNA or derivatives thereof.

The ribozymes of the present invention are distinct from the RNA endoribonuclease which occurs naturally in Tetrahymena Thermophila (known as the IVS, or L-19 IVS RNA) and which has been extensively described by Thomas Cech and collaborators (Zaug, A. J. et al, Science (1984) 224: 574–578; Zaug, A. J. and Cech, T. R., Science (1986) 231: 470–475; Zaug, A. J., et al, Nature (1986) 324: 429–433; published International patent application No. WO 88/04300 by University Patents Inc.). The Cech endoribonuclease has an eight base pair active site which hybridizes to a target RNA sequence whereafter cleavage of the target RNA takes place, with a requirement for free guanosine or guanosine derivatives. The fragments which arise from cleavage contain terminal 5' phosphate and 3' hydroxyl groups. The limited number of nucleotides available for hybridization to an RNA substrate limits the effectiveness or efficiency of the Cech endoribonuclease as in general, oligonucleotides comprising less than twelve nucleotides hybridize poorly to target sequences. It also appears that a number of nucleotides in the active site of the Cech endoribonuclease may need to be conserved for efficient endoribonuclease activity. This restricts the number of permutations of active site sequences which can be engineered to effect hybridization to target sequences, thereby restricting the range of RNA target sequences cleavable by the Cech endoribonuclease. The Cech endoribonuclease also modifies RNA by adding a free guanosine nucleotide to the 5' end of cleaved RNA.

In contrast, the ribozymes of the present invention hybridize efficiently to a wide range of target RNA sequences, and do not modify the cleaved target RNA.

The ribozymes of the present invention comprise a hybridizing region which is complementary in nucleotide sequence to at least part of a target RNA, and a catalytic region which is adapted to cleave the target RNA. The hybridizing region contains 9 or more nucleotides.

In a preferred aspect the ribozymes of the present invention have a hybridizing region comprising one or more arms formed of single stranded RNA and having a sequence complementary to at least part of a target RNA, said one or more arms being associated with a catalytic region capable of cleaving said target RNA; and where the hybridizing region comprises a single arm of RNA said arm contains at least 9 nucleotides, and where the hybridizing region comprises 2 or more arms of RNA, the sum of nucleotides in said arms is greater than 9 nucleotides.

In one embodiment of the invention, there is provided a ribozyme of the formula 1 (SEQ. I.D. No. 1):

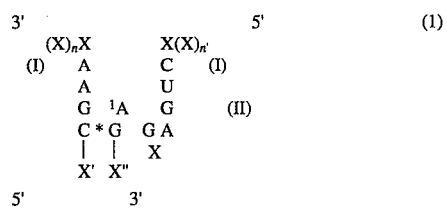

wherein;

X represents any ribonucleotide and each X residue may be the same or different; the sum of n and n' is greater than 6 and n and n' may be the same or different; an (*) represents a base pair between complementary ribonucleotides; X' and X" represent oligoribonucleotides of complementary sequence along at least part of their length to allow base pairing between the oligoribonucleotides, or X' and X" together form a single RNA sequence wherein at least part of said sequence comprises a stem formed by base pairing between complementary nucleotides; and optionally, an additional nucleotide selected from one of A, G, C or U may be inserted after ¹A in formula (1).

Region (I) of formula (1) represents the arms or flanking sequences of a ribozyme which hybridize to respective portions of a target RNA sequence. The arms may hybridize along the full length of the target RNA or part thereof. An RNA catalytic region is depicted at region (II) of formula 1. The catalytic region may contain one or more additional nucleotides which do not adversely effect catalytic activity. Such additions could be readily tested for ribozyme activity without undue experimentation following the teachings of the specification. The catalytic region may also form part of the hybridizing region.

The oligoribonucleotides X' and X" may comprise up to 5,000 or more nucleotides.

According to a further specific embodiment of the present invention there is provided a ribozyme of the formula 2 (SEQ. I.D. No. 2):

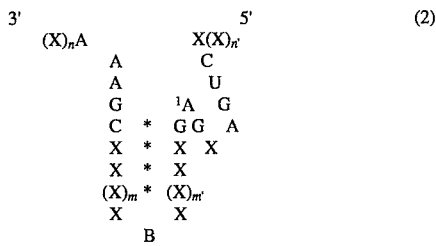

wherein;

X represents any ribonucleotide and each X residue may be the same or different;

an (*) represents a base pair between complementary ribonucleotides;

n and n' are as previously defined;

m and m' are 1 or more and may be the same or different;

B represents a bond, a base pair, a ribonucleotide, or an oligoribonucleotide containing at least 2 ribonucleotides;

and optionally, an additional nucleotide selected from any one of A, G, C or U may be inserted after $^1$A in formula (2).

The ribozymes of the present invention may be prepared by methods known per se in the art for the synthesis of RNA molecules. (For example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T7 RNA polymerase or SP6 RNA polymerase. A DNA sequence corresponding to a ribozyme of the present invention may be ligated into a DNA transfer vector, such as plasmid or bacteriophage DNA. Where the transfer vector contains an RNA polymerase promoter operably linked to DNA corresponding to a ribozyme, the ribozyme may be conveniently produced upon incubation with an RNA polymerase. Ribozymes may, therefore, be produced in vitro by incubation of RNA polymerase with an RNA polymerase promoter operably linked to DNA corresponding to a ribozyme, in the presence of ribonucleotides. In vivo, prokaryotic or eukaryotic cells (including mammalian and plant cells) may be transfected with an appropriate transfer vector containing genetic material corresponding to a ribozyme in accordance with the present invention, operably linked to an RNA polymerase promoter such that the ribozyme is transcribed in the host cell. Transfer vectors may be bacterial plasmids or viral RNA or DNA. Nucleotide sequences corresponding to ribozymes are generally placed under the control of strong promoters such as, for example, the lac, SV40 late, SV40 early, metallothionin, or λ promoters. Ribozymes may be directly transcribed in-vivo from a transfer vector, or alternatively, may be transcribed as part of a larger RNA molecule. For example, DNA corresponding to ribozyme sequences may be ligated into the 3' end of a carrier gene, for example, after a translation stop signal. Larger RNA molecules may help to stabilize the ribozyme molecules against nuclease digestion within cells. On translation the carrier gene may give rise to a protein, whose presence can be directly assayed, for example, by enzymatic reaction. The carrier gene may, for example, encode an enzyme.

In a further aspect of the invention, there is provided a DNA transfer vector which contains a DNA sequence corresponding to a ribozyme operably linked to a promoter to provide transcription of the ribozyme.

In one preferred method of producing a ribozyme, two synthetic oligonucleotides of complementary sequence are prepared by standard procedures (for example, using an Applied Biosystems Model 380A DNA Synthesizer (Applied Biosystems Inc., Foster City, Calif. 94404)), and hybridized together. One of the oligonucleotides encodes a desired ribozyme. The respective ends of the hybridized oligonucleotides correspond to different restriction enzyme sites, say EcorR1 at one end and Pst1 at the other end. After cleavage with appropriate restriction enzymes (EcoR1 and Pst1 in the above example), the double stranded DNA fragment may be cloned into a transfer vector. Where the plasmid vector contains an RNA polymerase promoter upstream from the DNA sequence corresponding to a ribozyme of the present invention. RNA transcripts corresponding to the ribozyme can be conveniently prepared either in-vitro or in-vivo. Where the ribozyme is comprised of two halves held together by base-pairing between complementary nucleotides, each half of the ribozyme may be produced according to the above methods, and the halves incubated together to form the ribozyme.

The preferred ribozymes of the present invention cleave target RNA which contains the sequence X°UY, where X° is any ribonucleotide, U is uracil and Y is adenine, cytosine or uracil. X°U forms part of a base pair flanking region and Y is not base paired. Preferably, but by no means exclusively, X° is guanidine, and X°UY is GUC or GUA. Any RNA molecule containing these sequences can be cleaved with the ribozymes of the present invention. Once the sequence of an RNA transcript containing the sequence X°UY has been determined, the arms of the ribozyme sequence can be synthesised to be complementary to, and thus hybridizable to, the RNA on the target sequence flanking the X°UY sequence. On hybridization of the arms of the ribozyme to the target RNA sequence flanking the X°UY sequence, the catalytic region of the ribozyme cleaves the target RNA within the X°UY sequence. RNA cleavage is facilitated in the presence of magnesium or other divalent cation at a pH of approximately 8.0.

Accordingly, the preferred ribozymes of the present invention can be engineered to cleave any RNA whose sequence is known. The high frequency of the residues cleaved by the ribozymes in RNA (1:64 for GUC in an RNA with random and equal frequency of base distribution) means that a number of potential sites for ribozyme cleavage can be confidently predicted in any given target RNA.

According to another aspect of the present invention there is provided a method for the inactivation of a target RNA sequence, which comprises reacting said target RNA sequence with a ribozyme of the present invention.

In-vivo, that is, within the cell or cells of an organism, a transfer vector such a bacterial plasmid or viral RNA or DNA, encoding one or more ribozymes, may be transferred into cells e.g. (Llwewllyn et al., J. Mol. Biol. (1987) 195: 115–123; Hanahan et al. J. Mol. Biol (1983) 166). Once inside the cell, the transfer vector may replicate, and be transcribed by cellular polymerases to produce ribozyme RNAs which then inactivate a desired target RNA. Alternatively, a transfer vector containing one or more ribozyme sequences may be transfected into cells or introduced into cells by way of micromanipulation techniques such as microinjection, such that the transfer vector or a part thereof becomes integrated into the genome of the host cell. Transcription of the integrated genetic material gives rise to ribozymes, which act to inactivate a desired target RNA.

The ribozymes of the present invention have extensive therapeutic and biological applications. For example, disease causing viruses in man and animals may be inactivated by administering to a subject infected with a virus, a ribozyme in accordance with the present invention adapted to hybridize to and cleave RNA transcripts of the virus. Such ribozymes may be delivered by parenteral or other means of administration. Alternatively, a subject infected with a disease causing virus may be administered a non-virulent virus such as vaccinia or adenovirus which has been genetically engineered to contain DNA corresponding to a ribozyme operably linked to an RNA promoter, such that the ribozyme is transcribed in the cells of the host animal, transfected with the engineered virus, to effect cleavage and/or inactivation of the target RNA transcript of the disease causing virus. The ribozymes of the present invention have particular application to viral diseases caused for example, by the herpes simplex virus (HSV) or the AIDS virus (HIV).

The ribozymes of the present invention also have particular application to the inactivation of RNA transcripts in bacteria and other prokaryotic cells, plants and animals. In bacteria, RNA transcripts of, for example, bacteriophage, which cause bacterial cell death, may be inactivated by transfecting a cell with a DNA transfer vector which is capable of producing a ribozyme in accordance with the present invention which inactivates the phage DNA. Alternatively, the ribozyme itself may be added to and taken up by the bacterial cell to effect cleavage of the phage RNA.

RNA transcripts in plants may be inactivated using ribozymes encoded by a transfer vector such as the Ti plasmid of *Agrobacterium tumefaciens*. When such vectors are transfected into a plant cell, the ribozymes are produced under the action of RNA polymerase and may effect cleavage of a specific target RNA sequence. Accordingly, plant viruses whose RNA sequence are known, or the RNA transcripts of plant genes, may be inactivated using ribozymes.

Endogenous gene transcripts in plants, animals or other cell types may be inactivated using the ribozymes of the present invention. Accordingly, undesirable phenotypes of characteristics may be modulated. It may, for example, be possible using the ribozymes of the present invention to remove stones from fruit or treat hereditry diseases in humans which are caused by the production of a deleterious protein, or over production of a particular protein.

The present invention will now be illustrated by way of non-limiting example only, with reference to the following non-limiting Examples, and Figures.

Figure 1D:
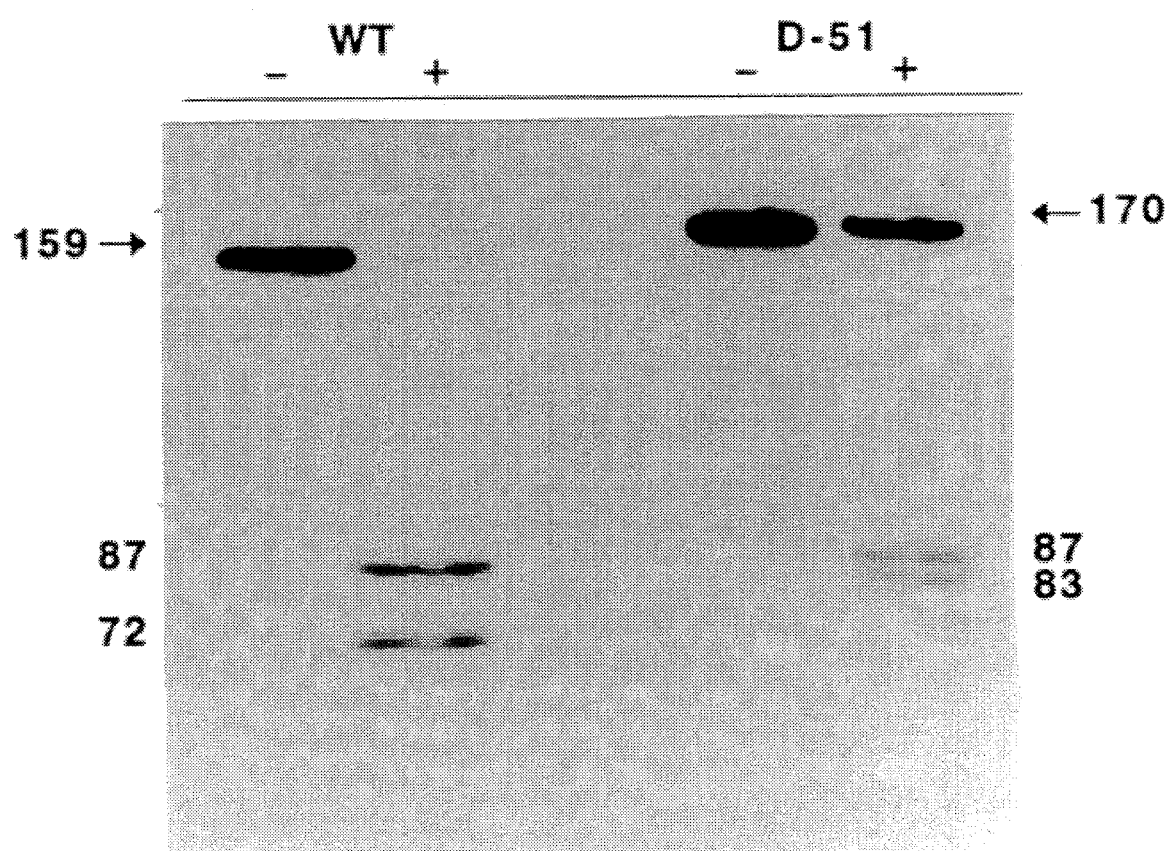
FIG. 1 shows RNA self cleavage sites of wild type and mutated RNAs; and an electrophoretic profile showing self-catalysed RNA cleavage products.

(a) Summarises the conserved structures associated with naturally-occurring RNA cleavage sites in ASBV, newt satellite DNA transcripts and the satellite RNAs of sTobRV, LTSV, velvet tobacco mottle virus, solanum nodiflorum mottle virus and subterranean clover mottle virus. Nucleotide sequences which are conserved between these structures are shown, while others are represented as X. Base-pairing is represented by "*" and the site for RNA cleavage is arrowed (Seq. ID No. 5-6).

(b) Shows the conserved nucleotide sequence associated with the cleavage of the (+) strand of sTobRV RNA. The cleavage site is arrowed (Seq ID No. 7)

(c) An in vitro mutant of sTobRV containing an insertion of eight nucleotides (shown boxed) together with a flanking duplication of three nucleotides (UGU resides 7 to 9) is shown (Seq. ID No. 8).

(d) Sub-cloned HaeIII fragments of wild type sTobRV and the D-51 in vitro mutant were each transcribed in both the (+) and (−) orientations and radiolabelled transcripts fractionated by polyacylamide gel electrophoresis. The positions of uncleaved 159 and 170 base transcripts from the wild type (WT) and mutant (D-51) sequences are arrowed; sizes of cleavage products are shown.

FIG. 2 shows the nucleotide sequence of a ribozyme and the products of ribozyme cleavage separated by gel electrophoresis.

(a) The inserted nucleotides in the D-51 mutant (FIG. 1c) contains a BamHI restriction endonuclease site. BamHI was used to split to mutant DNA, and the two sequences were sub-cloned and transcribed separately in vitro. The RNA transcripts are shown schematically, with potential base-pairings between the RNAs indicated "*". The fragment containing the arrowed site for cleavage is referred to as S-RNA, the fragment containing the ribozyme is designated Rz-RNA (Seq. ID No. 9-10).

(b) [$^{32}$P]-Rz-RNA (101 bases) was incubated alone (lane 1), and with unlabelled S-RNA (lane 2). [$^{32}$P]-S-RNA was incubated alone (lane 3), and with unlabelled and $^{32}$P labelled Rz-RNAs (lanes 4 & 5 respectively).

Figure 3:
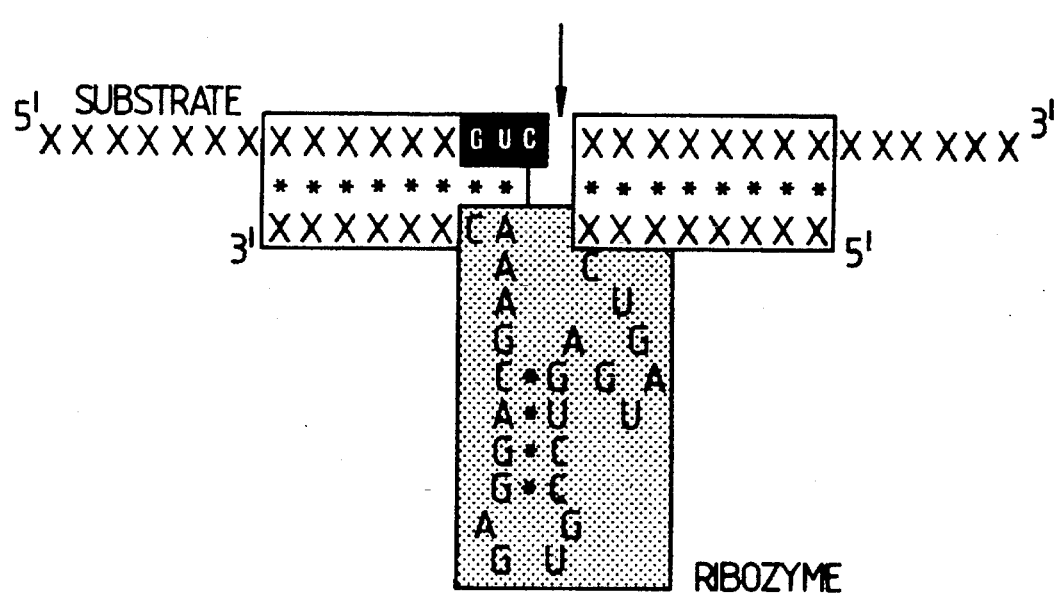
Figure 4A:
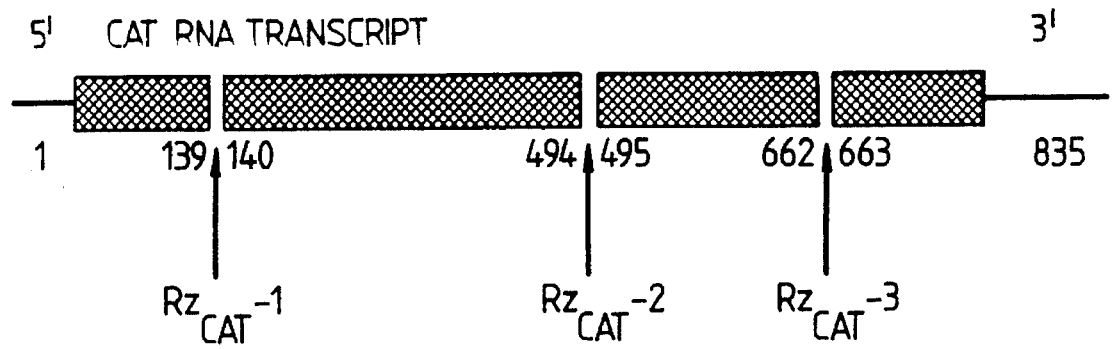
Figure 4B:
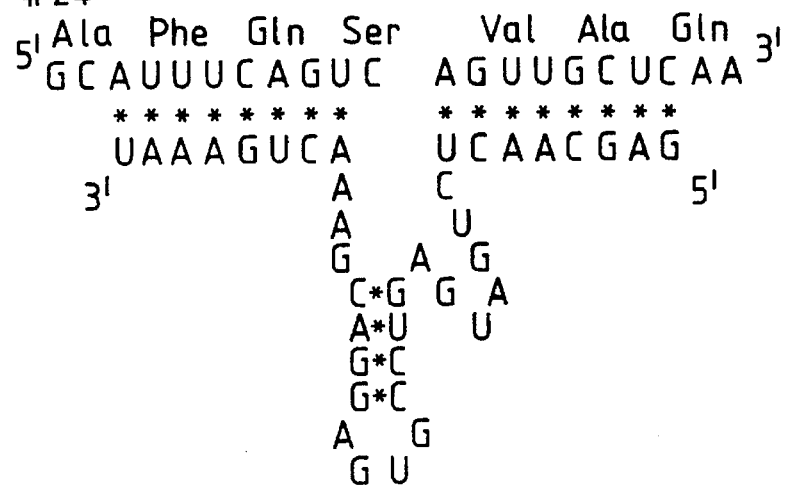
Figure 4C:
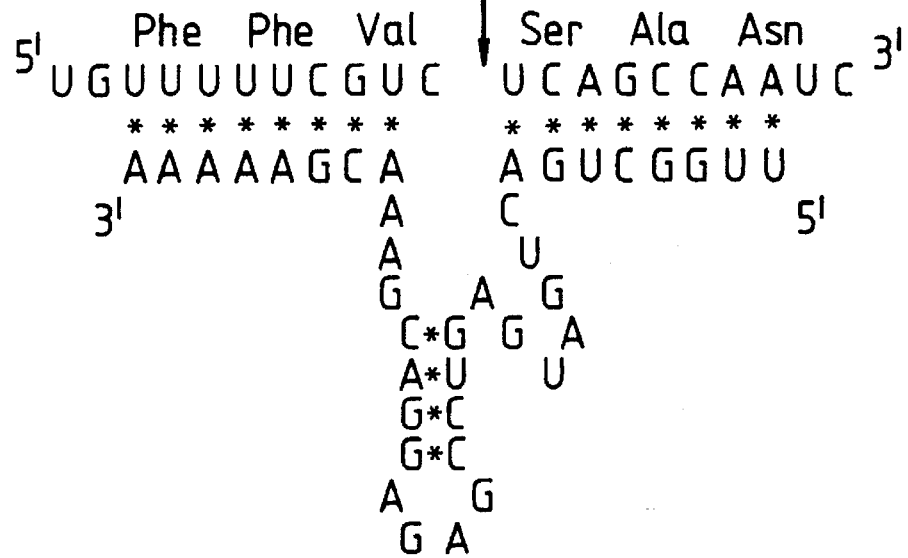
Figure 4D:
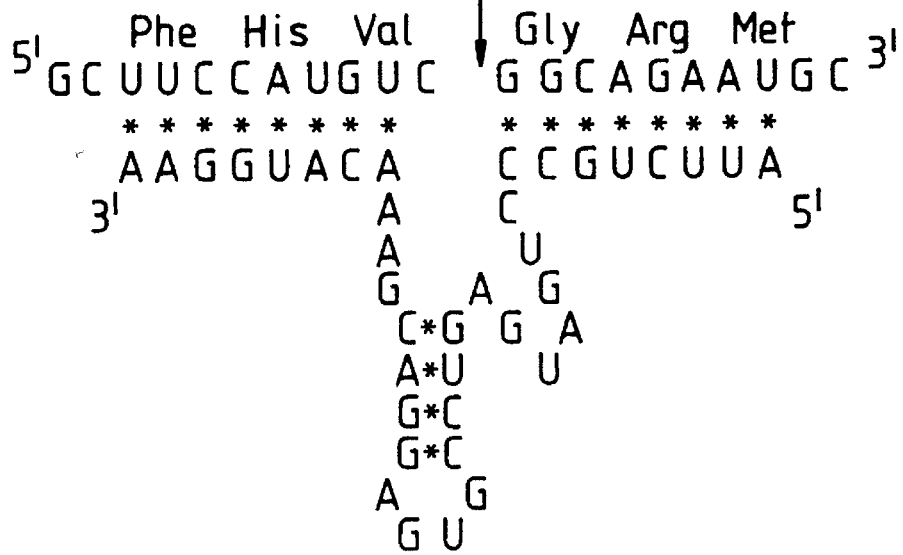

FIG. 3 shows a schematic model of a ribozyme according to one embodiment of the present invention. Region A represents the cleavage sequence within the target RNA. Region B represents a catalytic region, and regions C represent the arms of the ribozyme (Seq. ID No. 11-12).

FIG. 4 shows the design of ribozymes targeted against the CAT (chloramphenicol acetyl transferase) gene transcript. Ribozymes, termed RzCAT-1, 2 and 3, were targeted against three sites within an 835 base in vitro transcript of the CAT gene. The relative locations of the cleavage sites on the transcript are shown schematically with the flanking bases numbered (a). The three ribozyme sequences are shown ((b) to (d)) with their target sequences (Seq. ID No. 13-21). Amino-acid sequences of the CAT gene are numbered and the predicted sites for RNA cleavage arrowed. RzCAT-1 and 3 contain 24 base sequences derived from (+) strand sTobRV (region B, FIG. 3), while RzCAT-2 contains a single U-A change in this region.

Figure 5A:
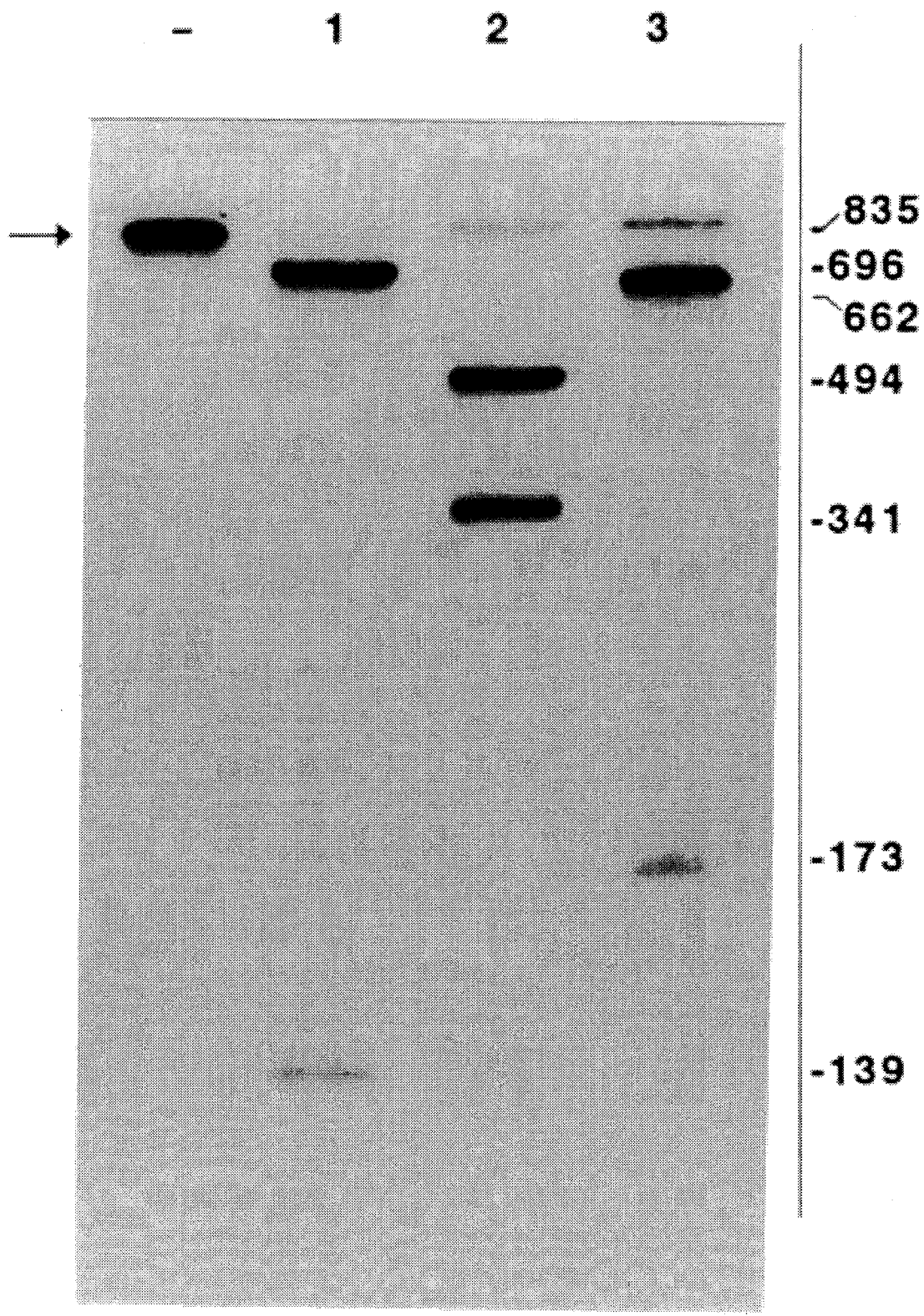

FIG. 5 shows the results of CAT RNA cleavage with ribozymes RzCAT-1 to 3.

(a) The [$^{32}$P]-CAT RNAs were gel fractionated after incubation alone (−) or with one of the three ribozymes, RzCAT-1 to 3 (lanes 1, 2 & 3 respectively). The location of full-length transcript is shown arrowed.

(b) 5' Terminal base analysis. The 3' fragments produced by ribozyme cleavage of CAT mRNA were [5'−$^{32}$P]-kinased, gel purified, subjected to complete nuclease digestion and the released terminal residues fractionated by pH 3.5 polyacrylamide gel electrophoresis. The 5' terminal nucleotides, determined by reference to markers (lane M), were A, U and G for the fragments produced by RzCAT-1 to 3 (lanes 1,2 and 3 respectively.

Figure 6A:
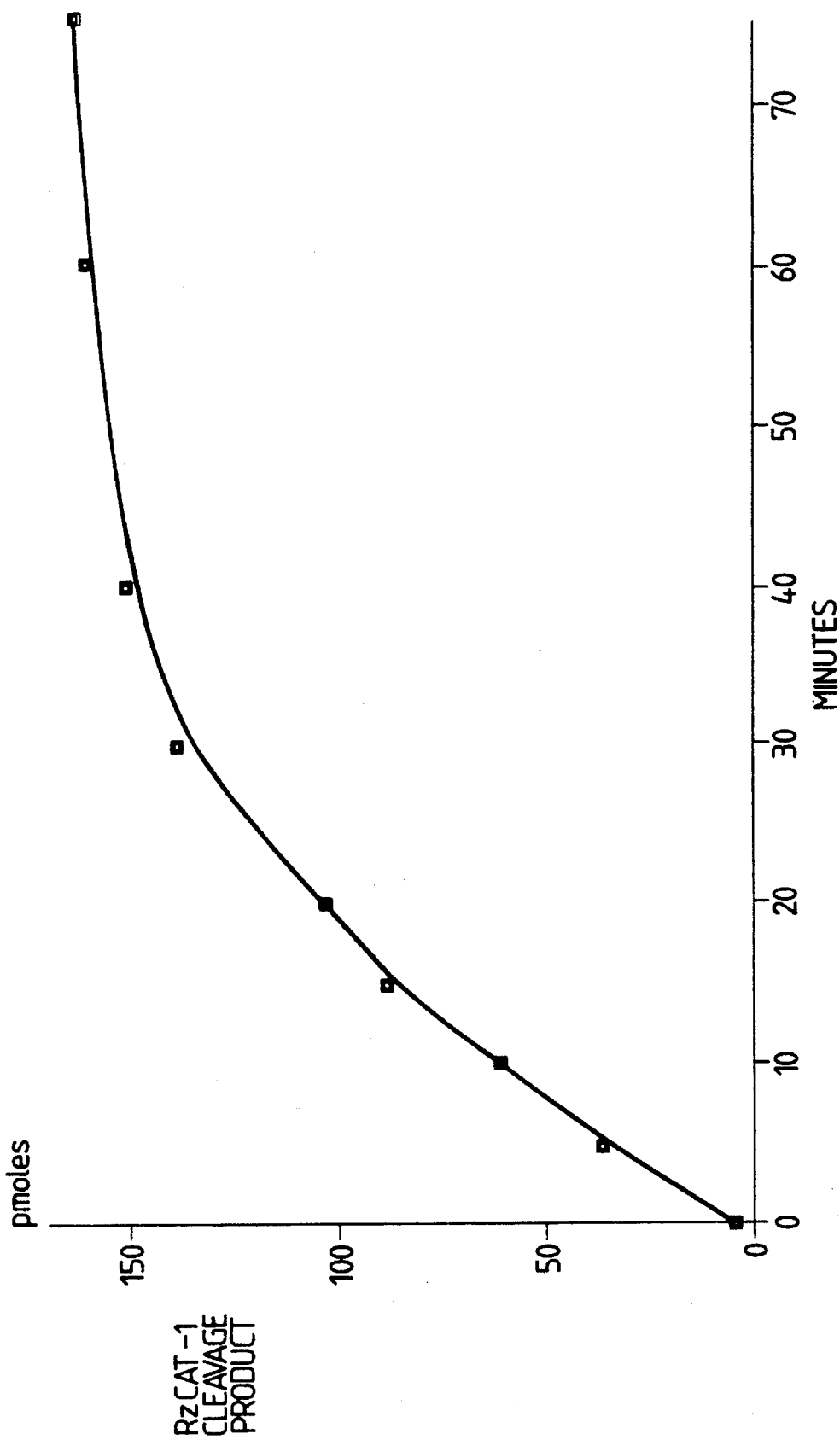
Figure 6B:
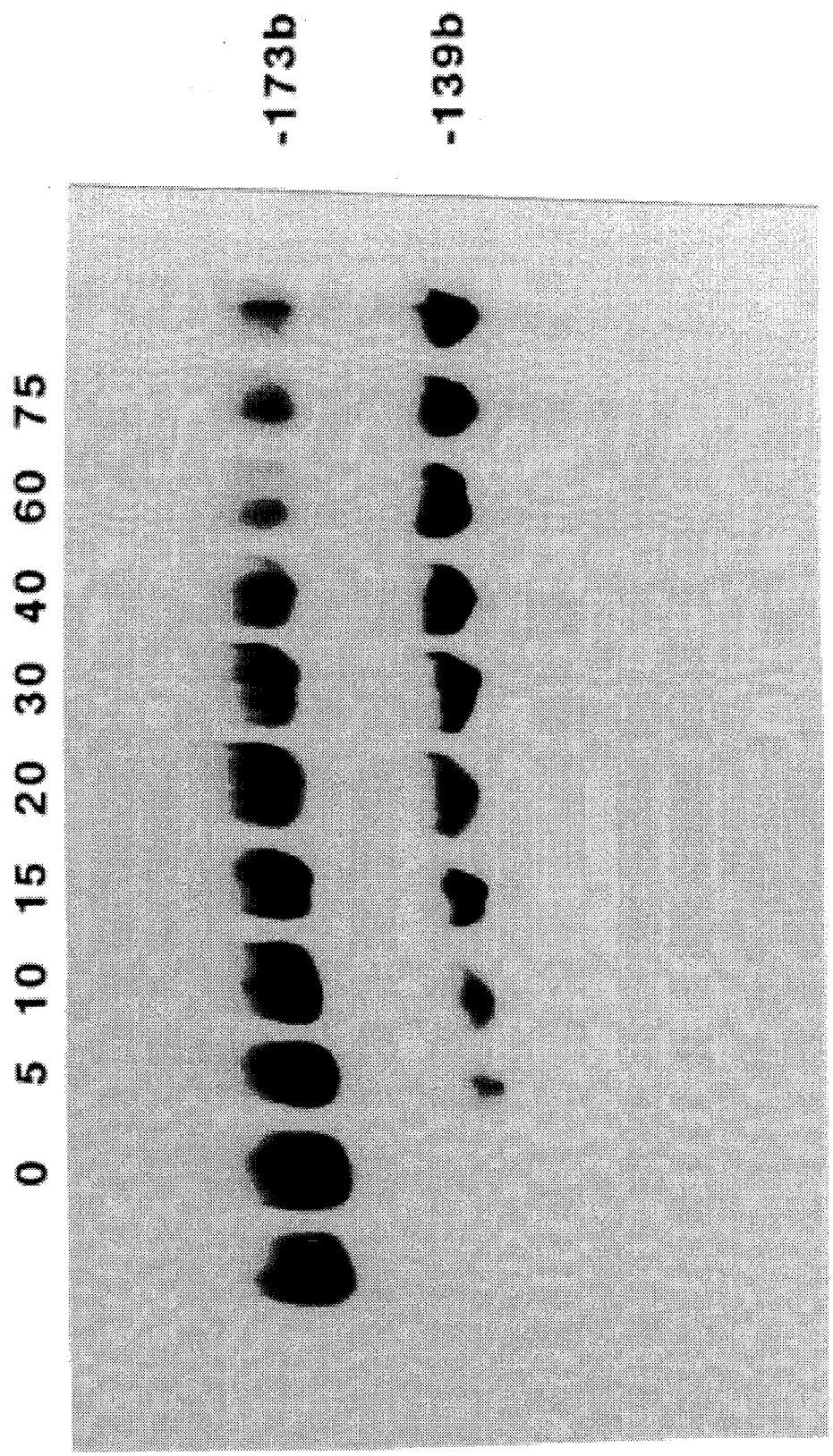
Figure 7A:
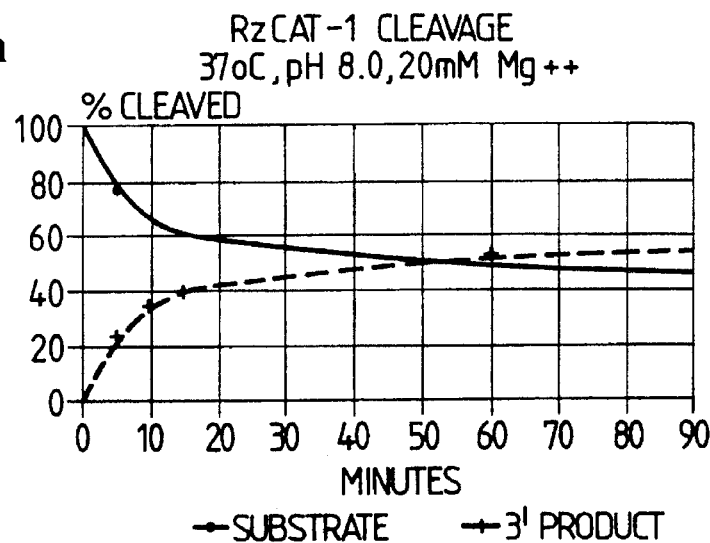
Figure 7B:
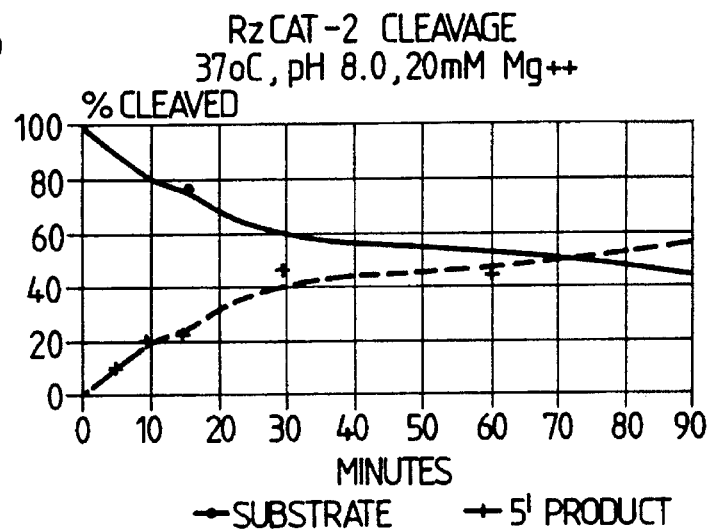
Figure 7C:
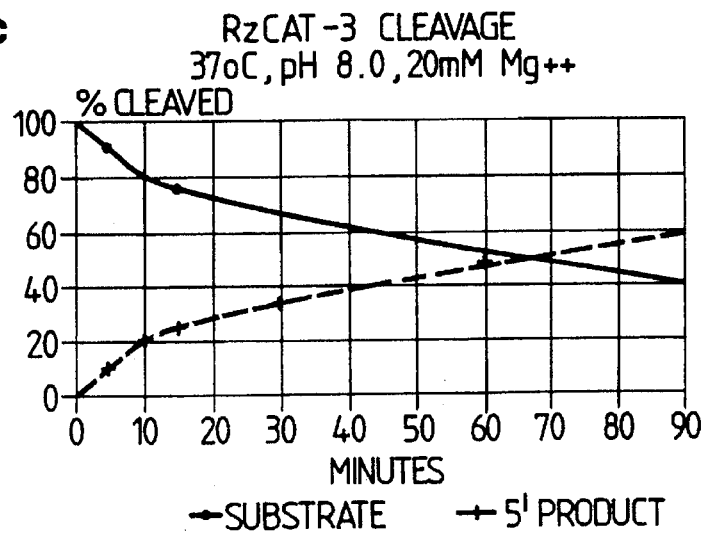
Figure 7D:
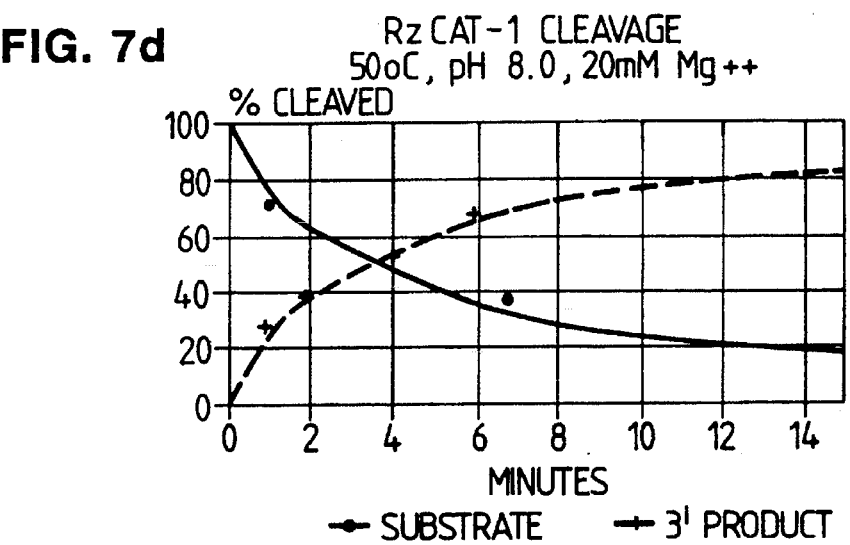
Figure 7E:
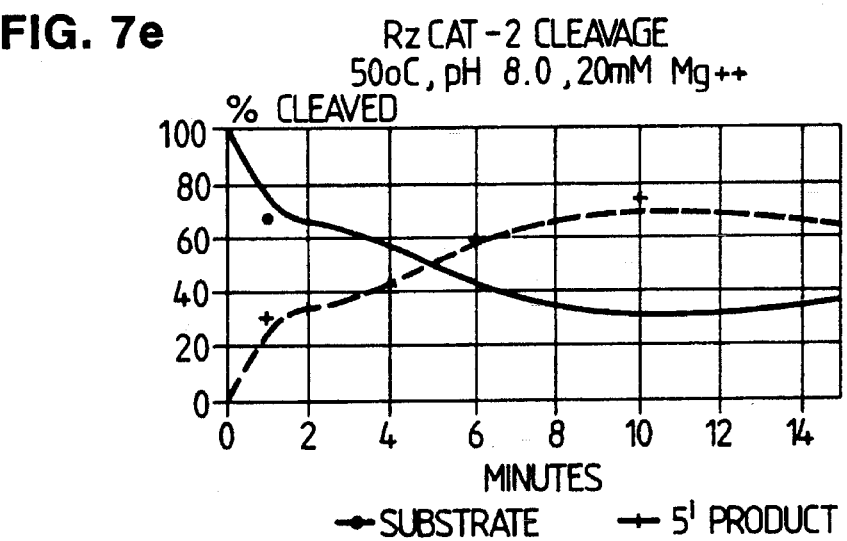
Figure 7F:
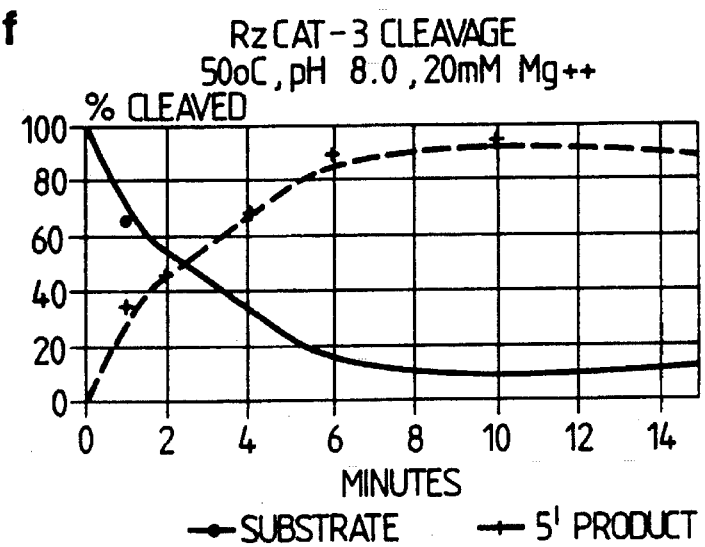

FIGS. 6a and 6b shows a time course of ribozyme (RzCAT-1) catalytic activity against CAT RNA. The amounts of the 139 nucleotide cleavage product were quantified and plotted. FIG. 6b shows the accumulation of the 139 base fragment with time, after polyacrylamide gel electrophoresis.

FIG. 7a–7f shows the relative rates of cleavage of CAT RNA under different temperature conditions. Substrate RNA is represented by a solid line. In each case cleavage product is represented by a broken line.

Figure 8A:
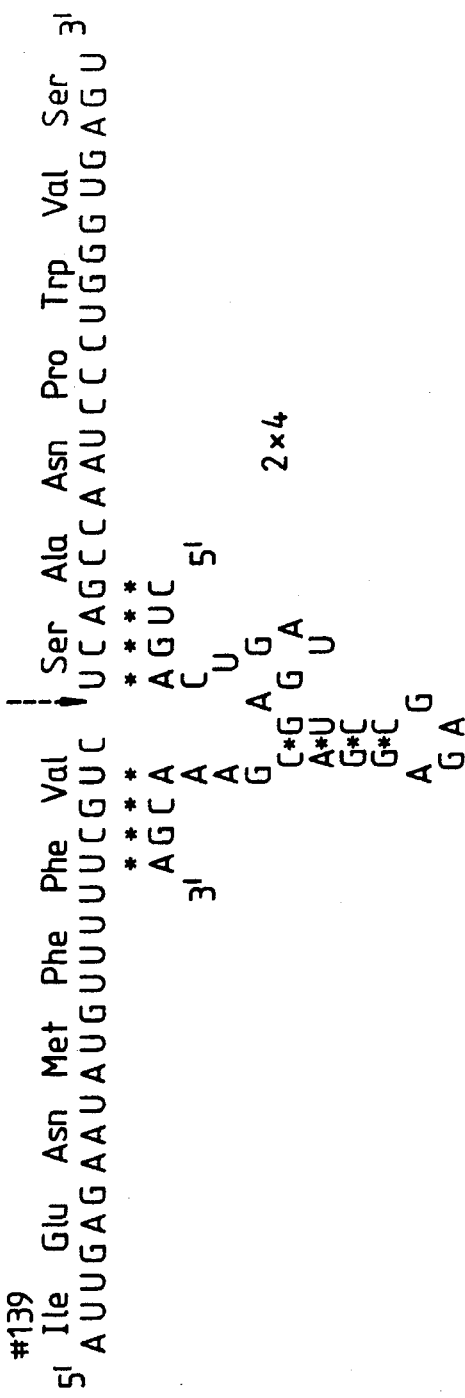
Figure 8B:
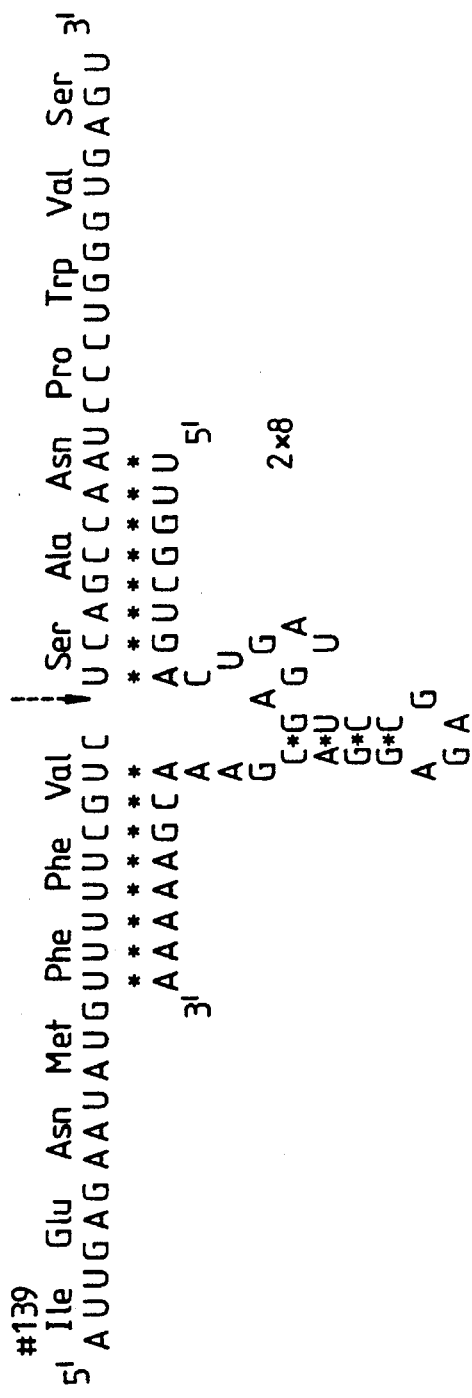

FIGS. 8a–8c depicts three ribozymes (corresponding to RzCAT-2) having arms or flanking sequence of varying length (Seq. ID No. 22–26)

Figure 9:
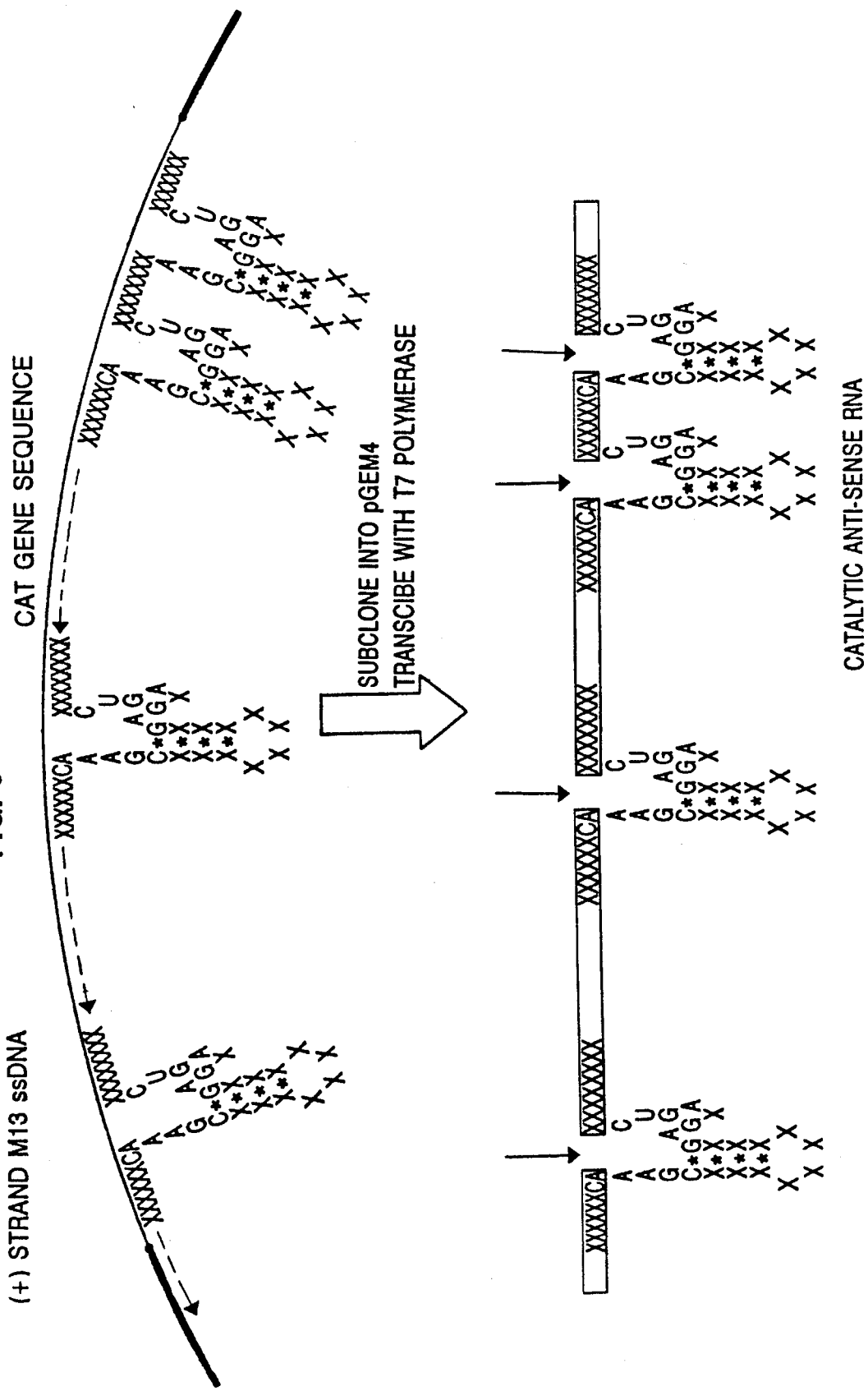

FIG. 9 depicts a scheme for producing a catalytic antisense RNA molecule having multiple catalytic domains. The CAT gene sequence contained in the (+) strand of M13 ssDNA is subcloned into pGEM 4 vector. The resulting recombinant is transcribed with T7 RNA polymerase to produce the catalytic anti-sense RNA.

Figure 10A:
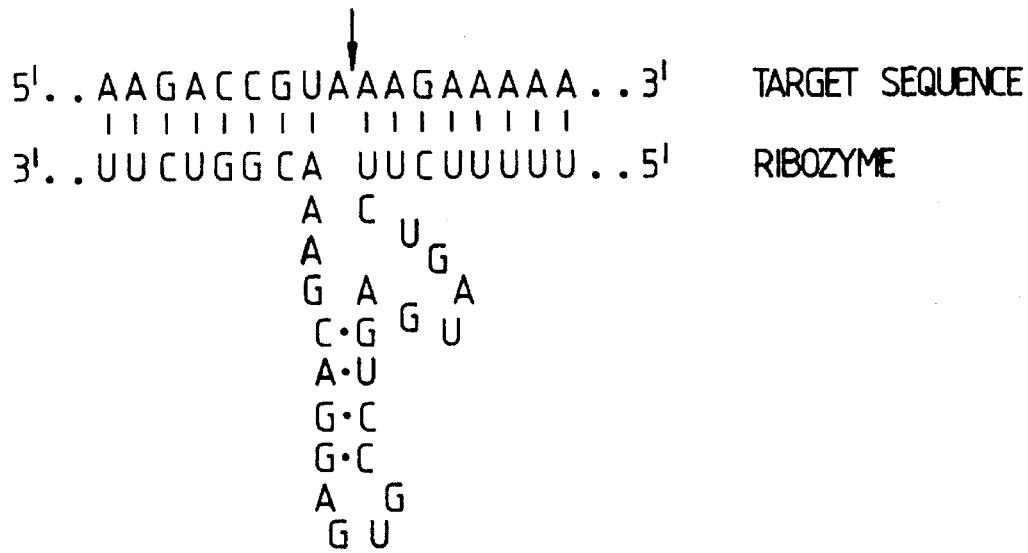
Figure 10B:
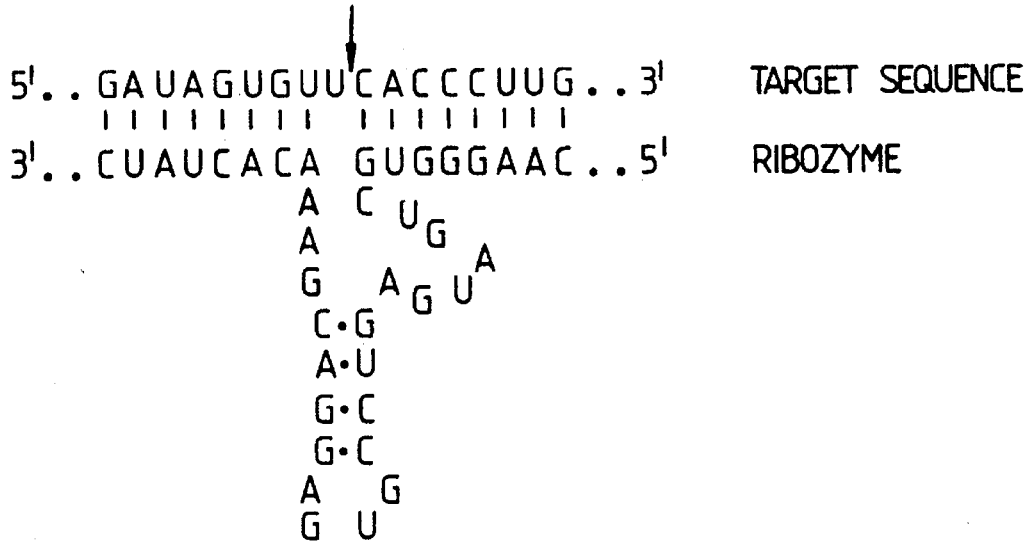

FIG. 10 shows ribozymes hybridizing to target sequences containing the GUA (10a) (Seq. ID No. 29–30) and GUU (10b) (Seq. ID No. 31–32) motifs in CAT mRNA.

FIG. 11 shows sites for self catalysed RNA cleavage in citrus exocortis viroid (CEV) RNA and its complement (Seq. ID No. 33–35).

FIG. 12 shows the ribozyme RzCEV25x(+) hybridized to target CEV RNA(a), and a gel electrophoretic profile of (+)CEV RNA and complementary (–) CEV RNA incubated with RzCEV25x(+) (b, lanes 1 and 2 respectively. Cleavage product is arrowed) (Seq. ID No. 36–37).

FIG. 13 shows the ribozyme RzCAT-2 hybridizing to its target sequence (a) and ribozyme RzSCMoV (b). The catalytic domain in each ribozyme is boxed. Differences in the catalytic region of RzSCMoV, when compared with RzCAT-2 are marked (Seq. ID No. 38,39,41).

FIG. 14 shows the ribozyme RzCEV-2 hybridizing to a target sequence in citrus exocortis viroid (CEV) RNA. The cleavage site corresponds to nucleotide-336 in the CEV RNA sequence. The alteration in nucleotide sequence in the catalytic domain, when compared with the catalytic domain of sTobRV, is circled (a) (Seq. ID No. 42–43). FIG. 14 (b) shows an electrophoretic profile of a control [(–) strand of CEV] RNA, lane 7 and the (+) strand of CEV RNA lane 8, after incubation with RzCEV2.

Figure 15A:
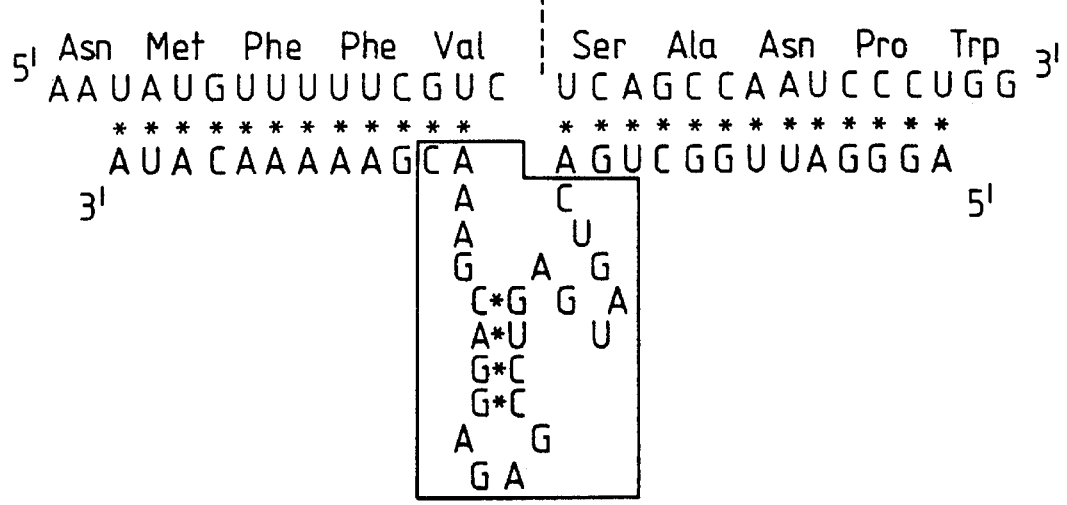
Figure 15B:
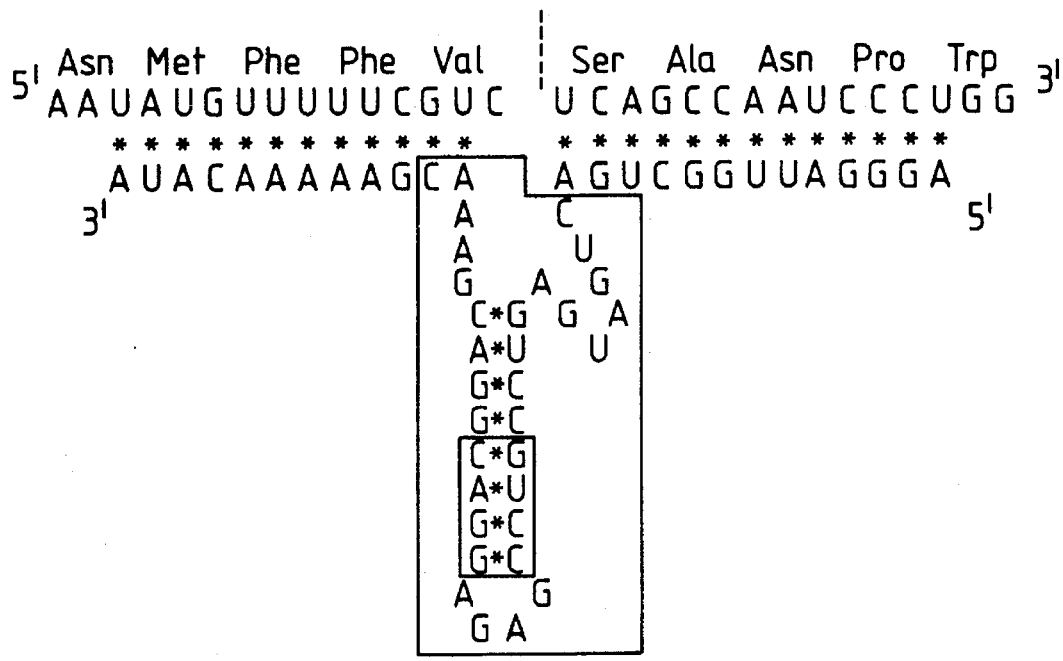

FIG. 15 shows the ribozyme RzCAT-2 (a) compared with ribozyme RzCAT-2B (b). Catalytic domains are boxed. Changes is the catalytic domain of RzCAT-2B compared with RzCAT-2 are also boxed (Seq. ID No. 38–40,44).

Figure 16:
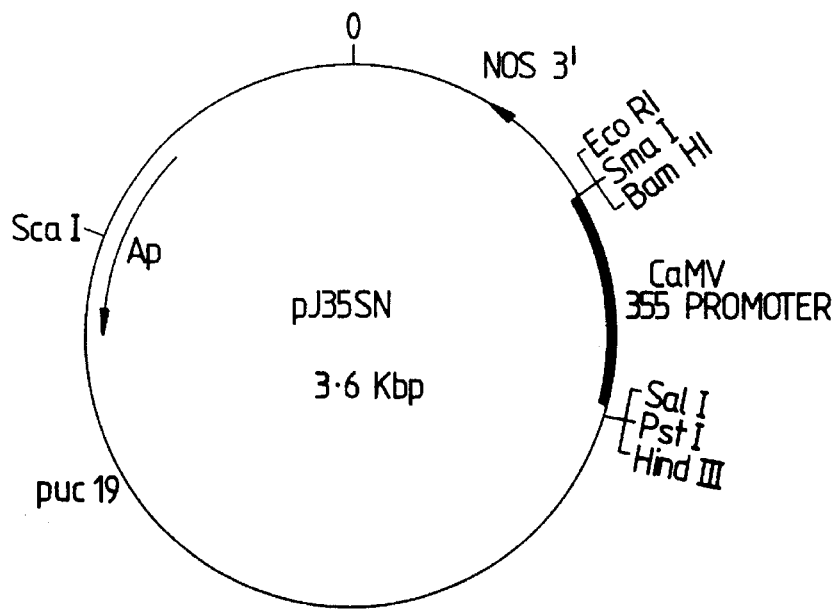

FIG. 16 shows a map of plasmid pJ35SN; and

Figure 17:
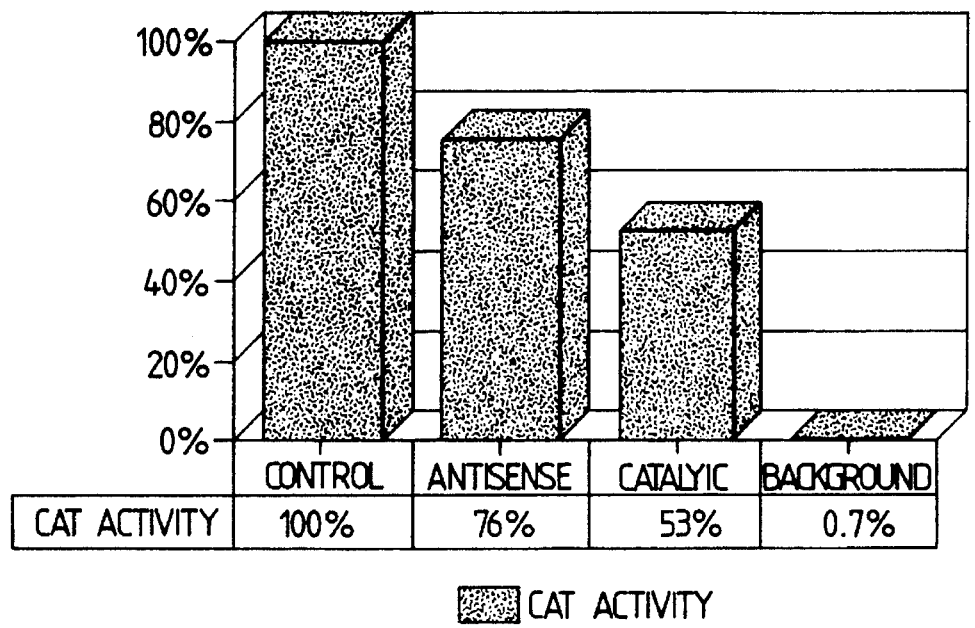

FIG. 17 is a graphic presentation of the average of four experiments on the inhibition of CAT expression in plants (tobacco protoplasts).

The following Examples are given to illustrate the present invention and are not to be construed as limiting the present invention.

Reactions and manipulations involving DNA, such as ligations, restriction enzyme digestions, bacterial transformation, DNA sequencing etc. were carried out according to standard techniques, such as those described by Maniatis et al (molecular Cloning, Cold Spring Harbour, 1982). Manipulations involving RNA were also carried out according to standard techniques, such as those described by Uhlenbeck (Nature 328, 596–600 (1987)) and Haseloff and Gerlach (Nature 334, 585–591 (1988)).

EXAMPLE 1

Self-Catalyzed Cleavage of Mutated sTobRV RNA:

A concensus of the domains associated with naturally-occurring RNA cleavage sites in ASBV, newt satellite DNA transcripts and the satellite RNAs of sTobRV, LTSV, velvet tobacco mottle virus (VMoV), solanum nodiflorum mottle virus (SNMV) and subterranean clover mottle virus (SCMoV) as shown in FIG. 1a. Nucleotide sequences which are conserved between these structures are shown, while non-conserved sequences are represented as X. An extra U is positioned after residue $^1$A in LTSV(+) strand.

The domain associated with the self-catalysed cleavage of the (+) strand of sTobRV was studied to ascertain the enzymic substrate activity within this domain. First, cloned sTobRV cDNAs were mutagenised using an oligonucleotide linker (BamH1) insertion protocol.

Construction of a Vector for in vitro Expression of sTobRV:

A 160 bp Taq 1-Spe 1 fragment of sTobRV cDNA was isolated from pSP653 (Gerlach et al. 1985, Virology 151: 172–185) and ligated to Acc 1-Spe 1 cut, phosphatase-treated pGEM 4 to reform the Acc 1 site. A resulting clone was linearized with Acc 1, phosphatase-treated and a 359 bp Taq 1 fragment of the sTobRV cDNA was inserted. The resulting clones were screened for the presence of a circularly permuted 520 bp sTobRV cDNA sequence containing the terminally redundant residues 277 to 81 (pTTS). The sTobRv sequence is flanked by promoters for T7 and SP6 RNA polymerases, and in vitro transcription gave rise to RNAs of (+) or (–) orientation which contained two sites for self-cleavage.

In vitro Mutagenesis:

The plasmid pTTS (50 ug) was linearized with BamH 1, treated with S1 nuclease and religated, to remove a unique BamH 1 site. The resulting construction, pTTS-B, was treated with $2 \times 10^{-4}$ units DNase 1 in 20 mM Tris-HCl pH 7.0, 15 mM $MnCl_2$ for 10 mins. at 37° C. The resulting linear DNAs were trimmed and/or end-filled using T4 DNA Polymerase, and purified by 0.7% LGT agarose gel electrophoresis and extraction. Kinased BamH 1 linker sequences (CGGATCCG) were ligated to the linearized plasmid overnight at room temperature in the presence of 5% polyethylene glycol. Subsequently, the reactions were BamH 1 digested, and the linear plasmid DNAs repurified by 0.7% LGT agarose gel electrophoresis (this was found necessary to remove last traces of circular plasmid, together with unligated linkers). Plasmids were recircularized using T4 DNA ligase and transformed into E. coli DH-1. Colonies (greater than 1000) were scraped from agar plates, grown in liquid culture to saturation and a mixed population of plasmid DNAs prepared. The mixed sTobRV cDNA inserts were excised by restriction enzyme digestion at flanking EcoR1 and Pst1 sites, purified by 1% LGT agarose gel electrophoresis, and sub-cloned into EcoR1-Pst1 cut, phosphates-treated pGEM 4. The resulting transformants were again pooled, grown in liquid culture and plasmid DNA prepared. The plasmid DNAs were treated with BamH1, to cleave only those plasmids containing a BamH1 linker sequence, and the linear forms were again purified by two rounds of 0.7% LGT agarose gel electrophoresis, recircularized with T4 DNA ligase, and transformed into E. coli DH-1. Individual transformants were screened for the approximate position of the inserted BamH1 linker within the sTobRV sequence by restriction enzyme digestion, subcloned into M13 mp19 and sequenced via the dideoxynucleotide chain termination technique.

A library of sTobRV mutants resulted, and nucleotide sequence analysis showed that each mutant contained an inserted BamH1 linker sequence (CGGATCCG) together with flanking duplicated or deleted sTobRV sequences. The mutants were transcribed in vitro and the RNAs assayed for their ability to undergo cleavage. From these experiments, a 52-nucleotide sequence was identified as containing both the substrate and cleavage portions of sTobRV RNA. This 52-nucleotide sequence, depicted in FIG. 1b, contained the domain of conserved sequence required for self-cleavage of other RNAs (FIG. 1a). One mutant, designated D-51, contained an eight nucleotide BamH1 linker sequence inserted between three duplicated sTobRV nucleotides numbered 7 to 9. This mutant underwent self-catalysed RNA cleavage.

97 and 108 base-pair HaeIII fragments containing the 52-nucleotide cleavage sequence of the wild type and D-51 RNAs (as shown in FIGS. 1b and 1c) were excised from sequenced plasmid clones. The fragments were ligated into the SmaI site of pGEM4 and screened to obtain both orientations of the insert. The plasmids were linearised using EcoR1 and (+) and (−) strand RNAs of lengths 159 and 170 bases were transcribed using 200 units/ml T7 RNA polymerase in 50 mM Tris-HCl, pH 7.5, 10 mM NaCl, 6 mM $MgCl_2$, 2 mM spermidine, 1000 units/ml RNasin, 500 μM ATP, CTP and GTP with 200 μM [$\alpha^{32}$P] UTP. RNAs were fractionated by electrophoresis on a 10% polyacrylamide, 7 molar urea, 25% formamide gel, and autoradiographed.

As shown in FIG. 1d, no cleavage of the (−) strand RNA transcripts was observed. This was as expected, as the (−) strand did not contain a self-catalysed cleavage site. With the (+) strands of both the wild type and D-51 sequences, cleavage took place, with cleavage of the D-51 RNA being somewhat less efficient than that of the wild type (FIG. 1d). This experiment indicates that the single stranded loop region at the right-hand side of the 52-nucleotide sequence involved in the self-catalysed cleavage of RNA is non essential.

Figure 2A:
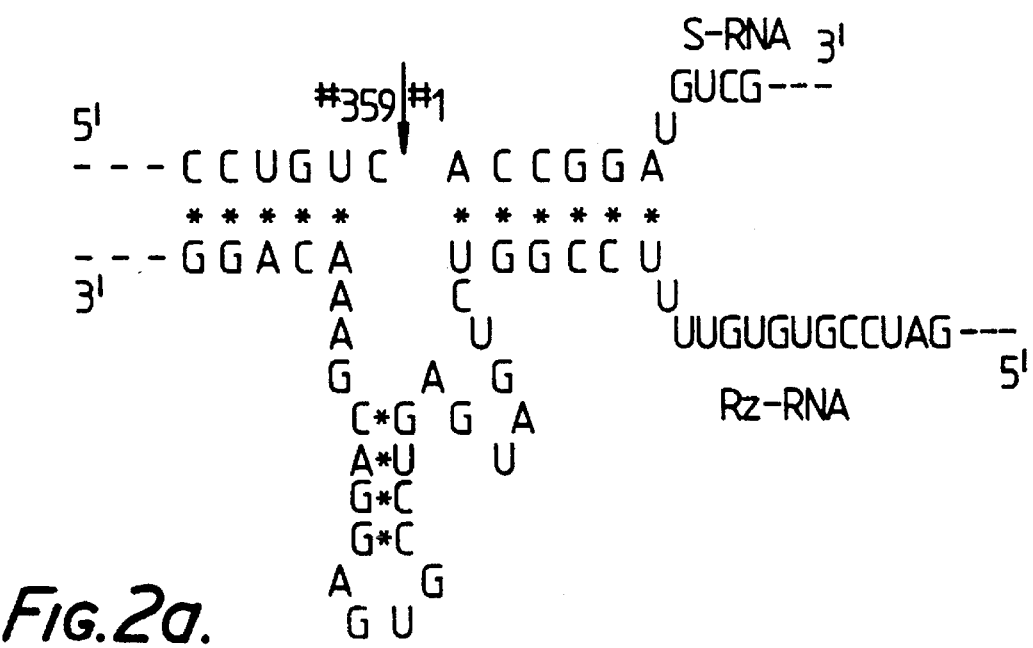

Separation of Enzymic and Substrate Activities:

Using the BamH1 restriction endonuclease site inserted into D-51, the flanking HaeIII-BamH1 and BamH1-HaeIII fragments were obtained and each was sub-cloned into an *E. coli* plasmid suitable for in-vitro transcription. This led to the elimination of the mutated single-stranded loop from the self-cleavage domain, splitting the region into two RNA segments (FIG. 2a). The smaller HaeIII-BamH1 fragment contained nucleotides 321 to 9, including the actual site of cleavage and was termed the S fragment. The BamH1-HaeIII fragment containing sTobRV nucleotides 7 to 48 was termed the ribozyme or Rz fragment. The *E. Coli* plasmids used for in-vitro transcription were pGEM3 and pGEM4 (Promega, Madison, Wis., U.S.A.). these expression plasmids contain:

(a) an origin of replication;

(b) selectable drug resistance (Amp$^r$) gene;

(c) a multiple cloning site flanked by RNA polymerase promoters which can be used for in vitro production of transcripts.

T7 DNA polymerase treated, Kpn1 digested Rz-pGEM3 and Xbal digested S-pGEM4 were transcribed using SP6 RNA polymerase under the same conditions as set out above.

Figure 2B:
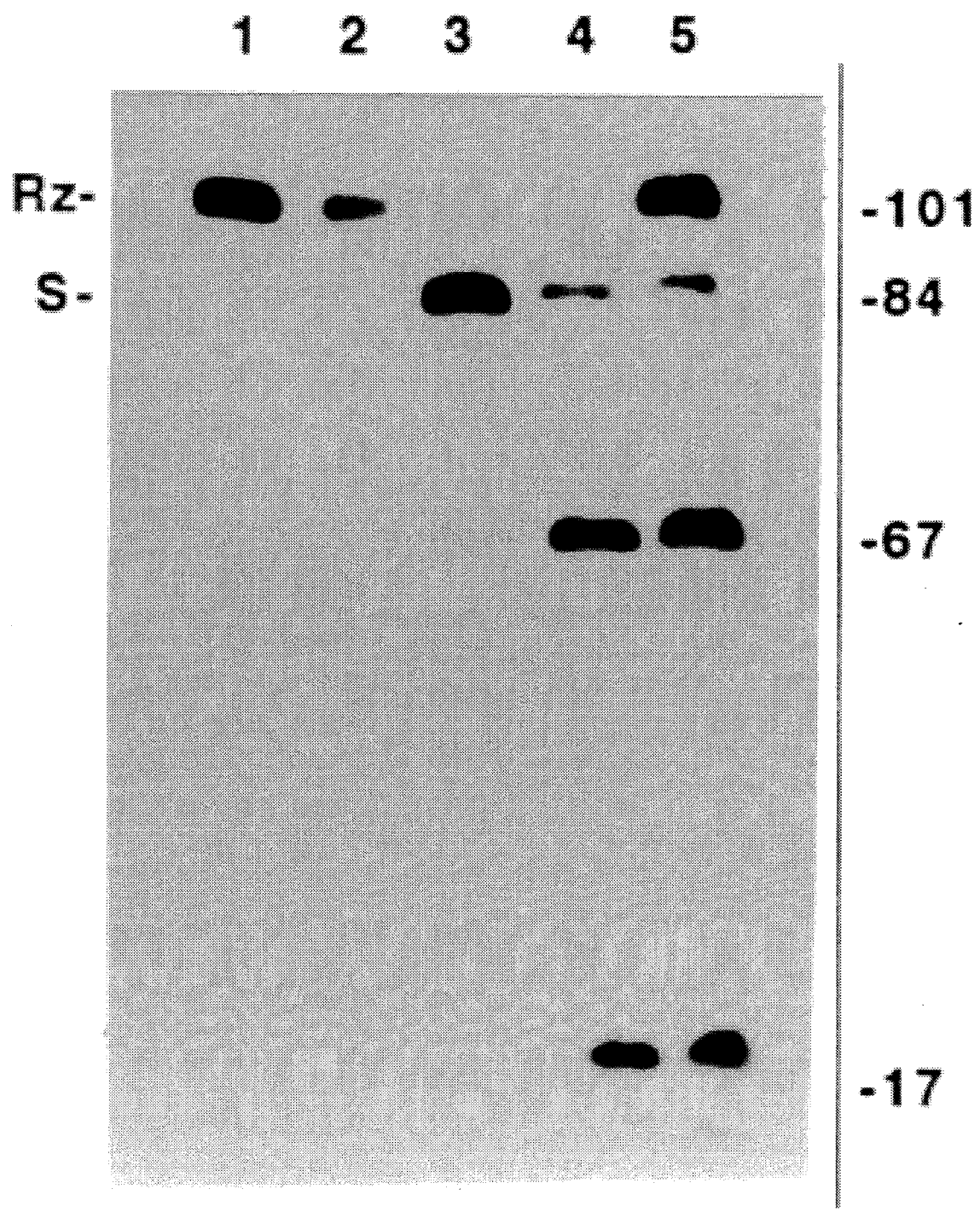

As shown in FIG. 2, both the S and Rz-RNAs showed no significant degradation when incubated alone (FIGS. 2b, lanes 1 and 3) under conditions suitable for highly efficient self-cleavage (50° C., 20 mM $MgCl_2$, pH 8.0). The labelled Rz-RNA also appeared unaltered after incubation with the S-RNA (FIG. 2b, lanes 2 and 5). However, when the S-RNA was mixed with the Rz-RNA, efficient cleavage of the S-RNA occurred (FIG. 2b, lanes 4 and 5) producing two fragments. The product sizes were consistent with cleavage of the S-RNA (84 bases) at the normal site between nucleotides #359 and #1, to give 5' and 3' proximal fragments of 67 and 17 nucleotides, respectively. This shows that the S-RNA acted as a substrate for ribonucleolytic cleavage by the Rz-RNA, which acted in a catalytic fashion.

A model of a ribozyme based on the catalytic region of sTobRV RNA is shown in FIG. 3. The ribozyme has two arms or flanking sequences of single stranded RNA shown at C, hybridizing to complementary sequences on a substrate RNA, i.e. RNA to be cleaved. Each flanking sequence shown at C, contains 8 ribonucleotides. The number of nucleotides contained in region C is not critical. Sufficient nucleotides must, however, be present to allow the ribozyme to hybridize to a target RNA. Four nucleotides in each region C appears to be the minimum number for hybridization.

The catalytic region B contains sequences which are highly conserved in naturally-occurring cleavage domains (see FIG. 1a). From a comparison with cleavage domains of the known sequences, the length of the base pair stem II is unimportant, as is the presence of an associated loop at one end thereof.

The cleavage site within the target RNA is depicted at A (in FIG. 3) as GUC. On the basis of our experiments (not shown), and others by Koizumi (FEBS LETT 288; 228–230 (1988); and FEBS LETT 239; 285–288 (1988)) on the cleavage sites in naturally occurring RNAs, the sequences GUA, GUC, CUC, AUC and UUC also act as cleavage sites within RNA.

EXAMPLE 2

Demonstration of the Design, Synthesis and Activity of Ribozymes with New and Highly Specific Endoribonuclease Activity:

As an illustration of this invention, three ribozymes have been designed, which are targeted against the transcript of a commonly used indicator gene derived from bacteria, Tn9 Chloramphenicol Acetyl Transferase (CAT), which can provide antibiotic resistance in bacteria, plants and animals and can be easily assayed. These ribozymes, designated RzCAT-1 to 3 correspond to potential GUC cleavage sites in CAT RNA at positions 139–140, 494–495 and 662–663 respectively. The sequences of these ribozymes are depicted in FIG. 4. In each case, the flanking sequences of the ribozyme which hybridize to the target CAT RNA, were 8 nucleotides in length. The catalytic region was chosen to correspond to that of sTobV RNA, shown in FIG. 3.

The CAT gene was obtained from pCM4 and sub-cloned as a BamH1 fragment into pGEM-32 (from Promega, Madison, Wis., U.S.A.). This plasmid was linearised with HindIII and CAT gene transcripts were obtained using T7 RNA polymerase with 220 uM [$\alpha$–$^{32}$P]UTP. Ribozyme sequences were synthesised as oligodeoxynucleotides, Rz CAT-1, 2 and 3, respectively. They were kinased, ligated with phosphatased treated, EcoRI-PstI cut pGEM4 and incubated with the Klenow fragment of DNA polymerase 1 before bacterial transformation. EcoRI linearised plasmids were transcribed with T7 RNA polymerase to produce ribozyme RNAs. Ribozymes were incubated with CAT transcript in 50 mM Tris-HCl pH 8.0, 20 mM $MgCl_2$ at 50° C. for 60 min, and the products fractionated by 5% polyacrylamide 7M urea, 25% formamide gel electrophoresis prior to autoradiography.

When the 840-nucleotide CAT transcript was incubated with any one of the three ribozymes, efficient and highly sequence-specific cleavage occurred (FIG. 5) producing 2 RNA fragments in each reaction. The fragment sizes were consistent with the predicted sites for cleavage (i.e. 139 and 696, 494 and 341, 662 and 173 base fragments were the 5' and 3' products from RzCAT-1 to 3 catalysed cleavage respectively). The conditions required for these ribozyme-catalysed cleavages were similar to those observed for naturally occuring cleavage reactions (Foster, A. C. and Symons, R. H., Cell 49: 211–220 (1987) and Foster, A. C. and Symons, R. H. Cell 50: 9–16 (1987)), with more efficient cleavage occuring at elevated pH, temperature and divalent cation concentrations (data not shown). When present in molar excess, the three ribozymes catalysed almost complete cleavage of the CAT RNA substrate after 60 min. in 50 mM Tris HCl, pH 8.0, 20 mM $MgCl_2$ at 50° C. Under similar conditions with 0.1 μM substrate and 3 μM ribozymes, the $T_{1/2}$ of CAT mRNA substrate was 3.5, 3.5 and 2.5 min. in the presence of RzCAT-1 to 3 respectively. The ribozyme sequences were inactive against the complement of the substrate RNA (i.e. the (+) strand), and in the form of oligodeoxyribonucleotides (data not shown). The 3' terminal cleavage fragments from each ribozyme catalysed reaction were isolated and 5' $^{32}$P-kinased (50 mM TrisHCl pH 9, 10 mM MgCl$_2$, 10 mM DTT with 50 uCi γ-$^{32}$P ATP and 5 units T4 polynucleotide kinase for 30 min. at 37° C.). Efficient kinasing of the fragments indicated that they possessed 5' terminal hydroxy groups, similar to those produced in naturally occuring cleavage reactions.

Figure 5B:
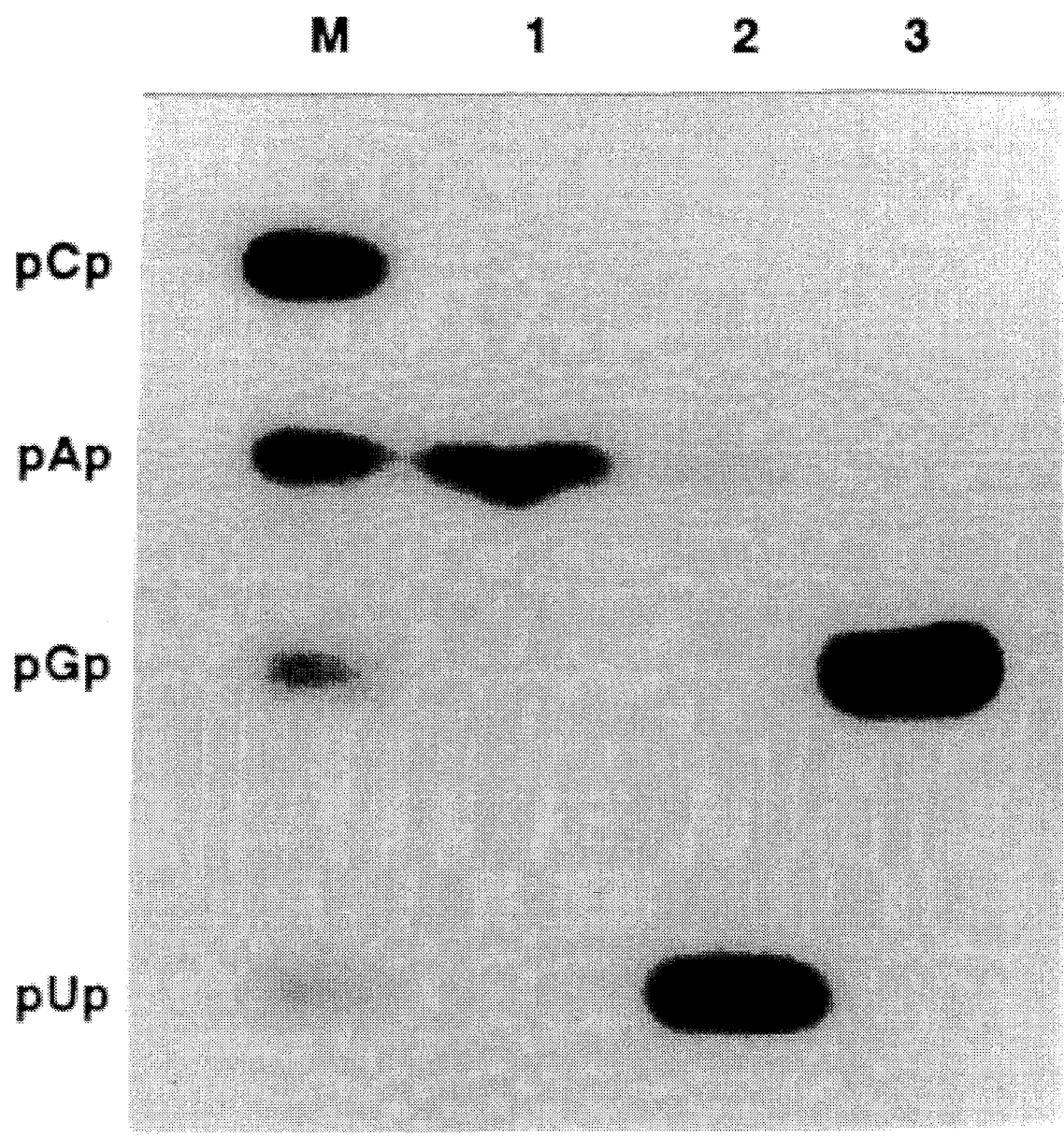

The terminal nucleotide of the fragments produced by cleavage of the CAT sequences by RzCAT-1 to 3 were determined. Briefly, radiolabelled fragments were purified on a 5% polyacrylamide gel and digested with an equal volume of 500 units/ml RNase T1, 25 units/ml RNase T2 and 0.125 mg/ml RNaseA in 50 mM ammonium acetate pH 4.5 for 120 min. at 37° C. The products were fractionated on a 20% polyacrylamide gel containing 25 mM sodium citrate, pH 3.5 and 7 molar urea. FIG. 5b shows that the cleavage of the CAT sequences by RzCAT-1 to 3 occurs precisely before nucleotides A, U and G respectively.

The terminal sequence of the CAT gene fragments were determined directly using the partial enzymatic digestion technique (Donis-Keller et al., Nucleic Acids Res. 4: 2527–2538 (1980)), using base-specific partial ribonucleolytic cleavage. The sequence of the fragments confirmed that cleavage occurred at the expected locations within CAT RNA (not shown).

Enzymatic Catalysis:

To demonstrate that ribozymes cause cleavage of the CAT mRNA substrate in a catalytic manner, each was incubated with a molar excess of substrate, under conditions which should favour both efficient cleavage and product dissociation. FIGS. 6a and 6b show the results of an experiment where after 75 min. at 50° C., pH 8.0 in 20 mM MgCl$_2$, 10 pmoles of RzCAT-1 had catalysed specific cleavage of 163 pmoles of a truncated CAT mRNA (173 bases) substrate to give 5' and 3' fragments of 139 and 34 bases, respectively. On average, each ribozyme had participated in greater than ten cleavage events. After 75 minutes at 50° C. some non-specific cleavage of RNA was noticed due to the extreme conditions, but 70% of the remaining intact RNAs (163 pmoles) had accumulated as the 139 base fragment. Similar results were obtained for RzCAT-2 and 3 (data not shown), and thus each acts as an RNA enzyme.

EXAMPLE 3

The Effect of Temperature on Ribozyme Activity:

The effect of reaction temperature on the in-vitro rate of ribozyme activity was examined.

A time course of reactions for ribozymes RzCAT-1 to 3 on CAT RNA substrate at 37° C. and 50° C. was carried out.

In this experiment, reactions for each ribozyme were set up in duplicate, using reaction conditions for ribozyme cleavage set out in Example 2. One reaction was incubated at 37° C., the other at 50° C. Samples were removed at time points to 90 minutes and the extent of reaction was analysed by denaturing polyacrylamide gel electrophoresis. FIGS. 7a–7f shows the time course of reaction for each of the ribozymes RzCAT-1 to 3 at 37° C. and 50° C. The reaction rate of each ribozyme increases with increased reaction temperature.

The time taken for 50% (t$_{1/2}$) cleavage of CAT RNA is set out in Table 1.

TABLE 1

|  | RzCAT-1 | RzCAT-2 | RzCAT-3 t½ (mins.) |
|---|---|---|---|
| 50° C. | 3.5 | 3.5 | 2.5 |
| 37° C. | 55.0 | 70.0 | 65.0 |

As shown in Table 1, the rate of reaction of ribozymes at 37° C. is approximately 20 times slower than the rate of reaction at 50° C.

EXAMPLE 4

The Effects of Varying Arm Lengths of Ribozymes (or Flanking Sequence) on Ribozyme Catalytic Activity:

The arms or flanking sequences of a ribozyme (region (I) of formula 1) hybridize the ribozyme to a target RNA whereafter cleavage of the RNA takes place. In this experiment, the effect on cleavage rate of a target sequence by altering the extent of complementarity and subsequent length of base pairing of the ribozyme arms to the target sequence was investigated.

Ribozymes were produced with 4, 8 and 12 base complementarity to the target sequence RzCAT-2 on each arm (FIGS. 8a–8c). The ribozymes were prepared according to the methods of Example 2. Ribozyme activity was determined by incubating the ribozyme RNA with CAT RNA as described previously.

The ribozyme having a 4 base complementarity on each arm did not cleave the substrate RNA. The ribozyme with 8 base complementarity on each arm cleaved the CAT substrate as did the ribozyme having 12 base complementarity. Ribozymes with 12 base complementarity cleaved target RNA more efficiently, as judged by reaction rate in-vitro than did ribozymes having a lesser number of base complementarities. Even though it appears necessary to have more than four base complementarity, increasing the length of the hybridizing region of ribozymes increases their reaction rate.

In a second experiment, the reaction efficiency of a ribozyme having (a) complementarity to the entire length of the CAT transcript target RNA and (b) multiple catalytic domains, was investigated.

Four GUC target sites in CAT RNA sequences were chosen. Ribozyme catalytic domains against these sites were "inserted" into a complete anti-sense (−) sequence for the CAT transcript and catalytic activity tested.

The four sites chosen were the three specified by RzCAT-1 to 3 described previously, and a further site which may be represented as follows (Seq. ID No. 3–4).

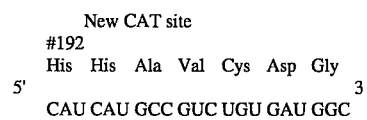

where "192" refers to amino acid 192 in the CAT polypeptide and an refers to the site of cleavage.

Oligodeoxyribonucleotides containing ribozyme catalytic domains and spanning each of these cleavage sites were used for M13 mutagenesis experiments to produce a sequence containing the entire complement of the CAT sequence but with the four ribozyme catalytic domains inserted within it. M13 mutagenesis was performed by binding of oligonucleotides containing ribozyme insertions to single stranded M13 DNAs containing uracil, followed by synthesis of complementary DNAs containing the insertion. The complementary DNAs were recovered following cloning in an appropriate *Escherichia coli* strain, (T. A. Kunkel 1985, Proc. Natl. Acad. Sci. U.S.A. 82: 488–492). The resultant double-stranded cDNA was cloned in an in-vitro expression vector to produce ribozyme RNA using the T7 polymerase transcription system. Ribozyme activity was determined by incubation of ribozyme RNA with CAT transcript followed by gel electrophoresis of the reaction mixture, after glyoxal treatment to denature nucleic acids.

Autolytic cleavage occurred at all the expected sites on the CAT transcript. Accordingly, the flanking sequences of arms or a ribozyme may extend along the full length of the RNA transcript which is to be cleaved.

FIG. 9 schematically shows the production of catalytic anti-sense RNA containing each of the four ribozymes. The catalytic anti-sense RNA contains approximately 900 bases.

Under the above reaction conditions, the ribozyme and target sequences form high molecular weight complexes presumably by extensive base pairing. A strong denaturing treatment such as glyoxal treatment is required to resolve reaction products during electrophoresis.

EXAMPLE 5

Target Sequences for Ribozyme Cleavage:

The GUA motif in mRNA was tested to see whether a ribozyme would effect RNA cleavage at this sequence.

A specific site in CAT mRNA, including the GUA motif (FIG. 10a) was chosen and an appropriate ribozyme sequence was prepared and tested for activity. The ribozyme contained arms of 8 ribonucleotides.

Synthetic oligonucleotides corresponding to the ribozyme of FIG. 10 were prepared according to Example 2 and double-stranded cDNA cloned into an in-vitro expression vector (pGEM 4, see above) in E. coli in order to produce ribozyme RNA using the T7 polymerase transcription system. Ribozyme activity was determined by incubation of ribozyme RNA with CAT mRNA, followed by gel electrophoresis of the reaction mixture as previously described.

The ribozyme effected cleavage at the GUA target site (not shown). Accordingly, the motif GUA in RNA is a substrate for ribozymes of the present invention. This was not completely unexpected since one naturally occuring cleavage site in the satellite RNA of lucerne transient streak virus requires recognition of a GUA site.

Similarly, a GUU motif in the CAT RNA target sequence was tested with an appropriate ribozyme (See FIG. 10b), and cleavage was effected.

EXAMPLE 6

Ribozyme Cleavage of Viral RNA:

Viroid RNA, in the form of citrus exocortis viroid RNA, was cleaved using a ribozyme of the present invention.

Two GUC target sites were chosen in citrus exocortis viroid (CEV) RNA. One site in the complementary strand sequence was also chosen. Ribozymes were prepared against all of these sites and tested for activity. The ribozymes were designated CEV9x(+), CEV9x(−) and CEV25x(+). FIG. 11 shows the three cleavage sites in CEV RNA for each of these ribozymes.

Ribozymes were prepared according to previous methods. Ribozyme RzCEV25x(+) is shown in FIG. 12. This ribozyme cleaves the GUC motif at nucleotide 116 of CEV RNA.

Figure 12B:
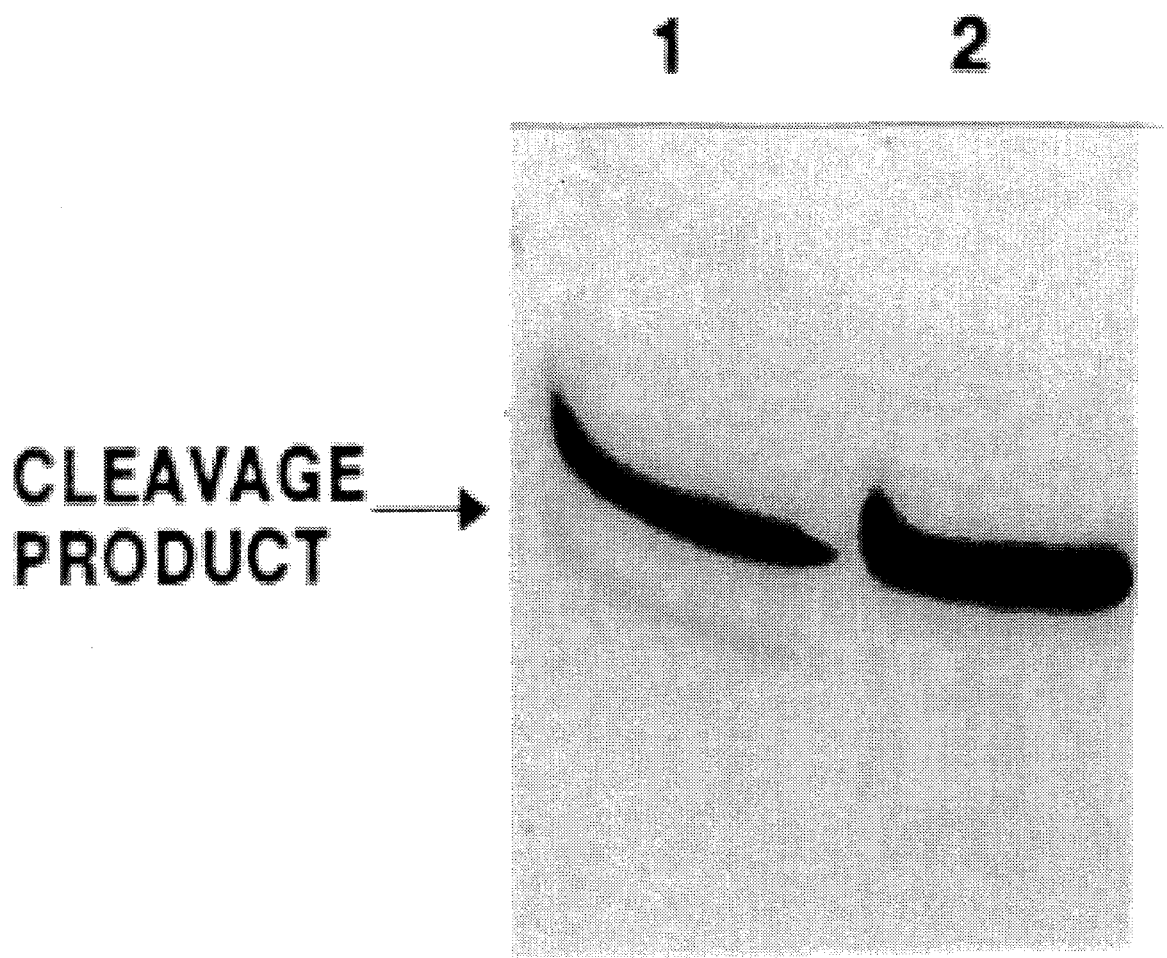

FIG. 12(b) shows cleavage of CEV RNA with ribozyme RzCEV9x(+). No cleavage is observed with ribozyme RzCEV9x(−).

This experiment indicates that ribozymes are active against target RNA sequences from diverse sources. This is to be expected, as all RNAs are formed from the basic ribonucleotide building blocks of adenine, guanine, cytosine and uracil, regardless of their animal, plant or microbial origin.

EXAMPLE 7

Examples of Ribozymes Having Variable Catalytic Domains

Figure 13A:
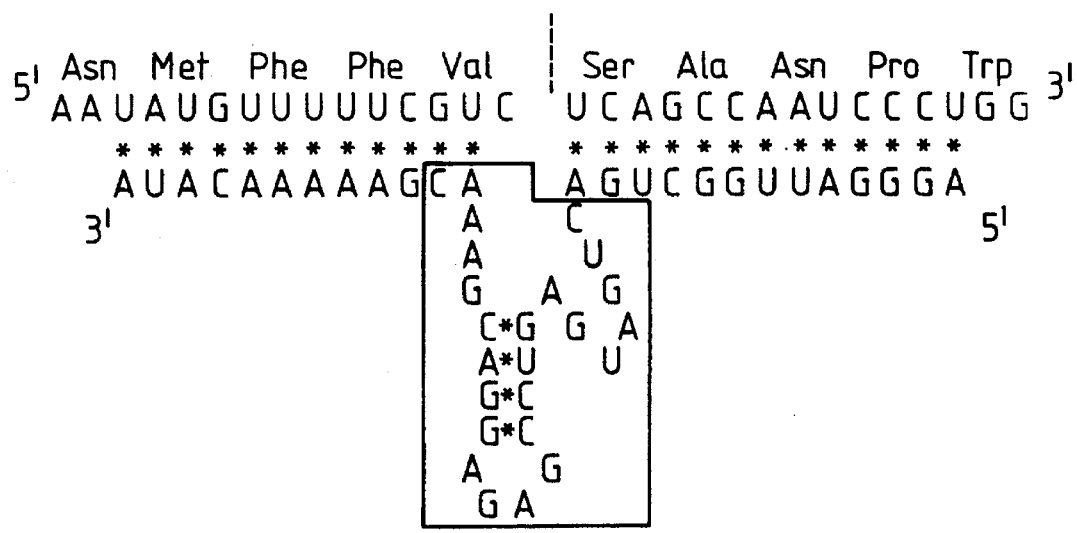
Figure 13B:
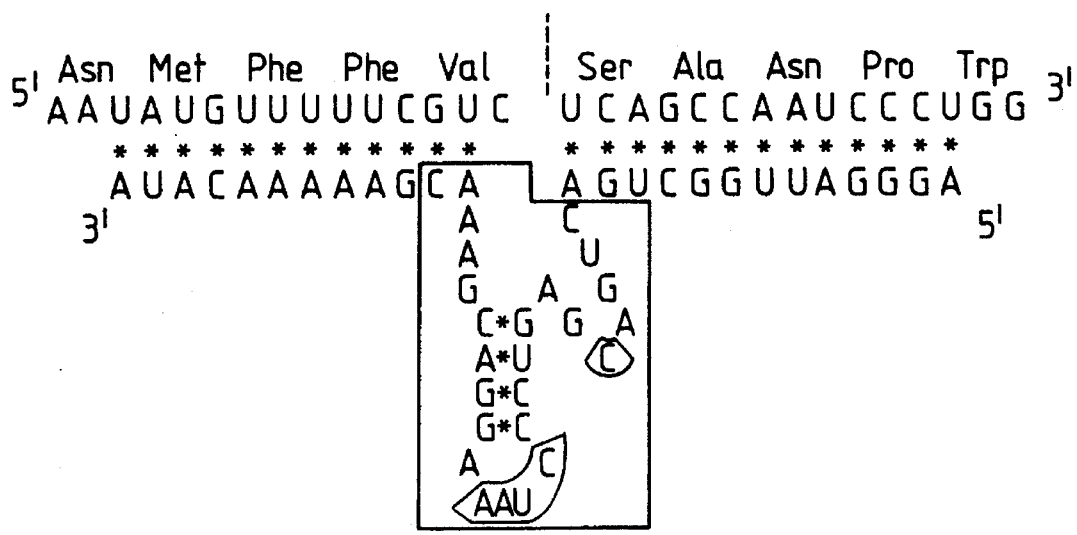

A ribozyme targeted against a CAT-2 site was prepared using the catalytic domain sequence from the satellite RNA of subterranean clover mottle virus (SCMoV). Twelve base complementarity of ribozyme arm flanking sequence was incorporated into the design of the ribozyme RzSCMoV. The ribozymes RzCAT-2 and RzSCMoV are shown at FIGS. 13a and 13b respectively. The loop region of RzSCMoV contains 5 nucleotides, having the sequence AAAUC. This is to be contrasted with the loop region of RzCAT-2 which contains 4 nucleotides having the sequence AGAG. In addition, RzSCMoV contains a C in the catalytic region, in place of U* in RzCAT-2. The different sequences in RzSC-MoV when compared with RzCAT-2 are marked.

The RzSCMoV was produced according to Example 2. RzSCMoV was active, yielding two cleavage products as expected.

Figure 14A:
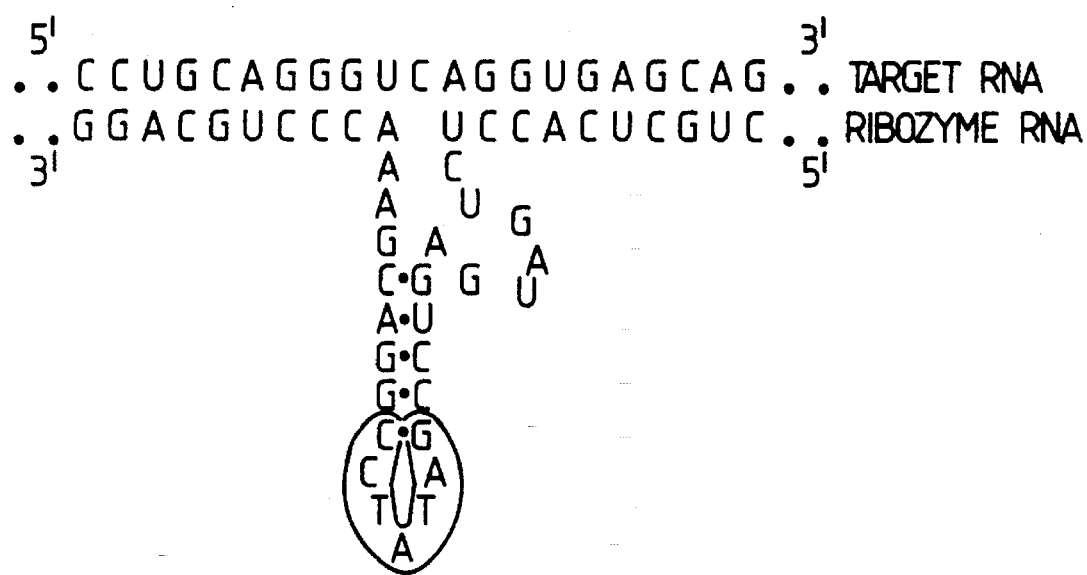
Figure 14B:
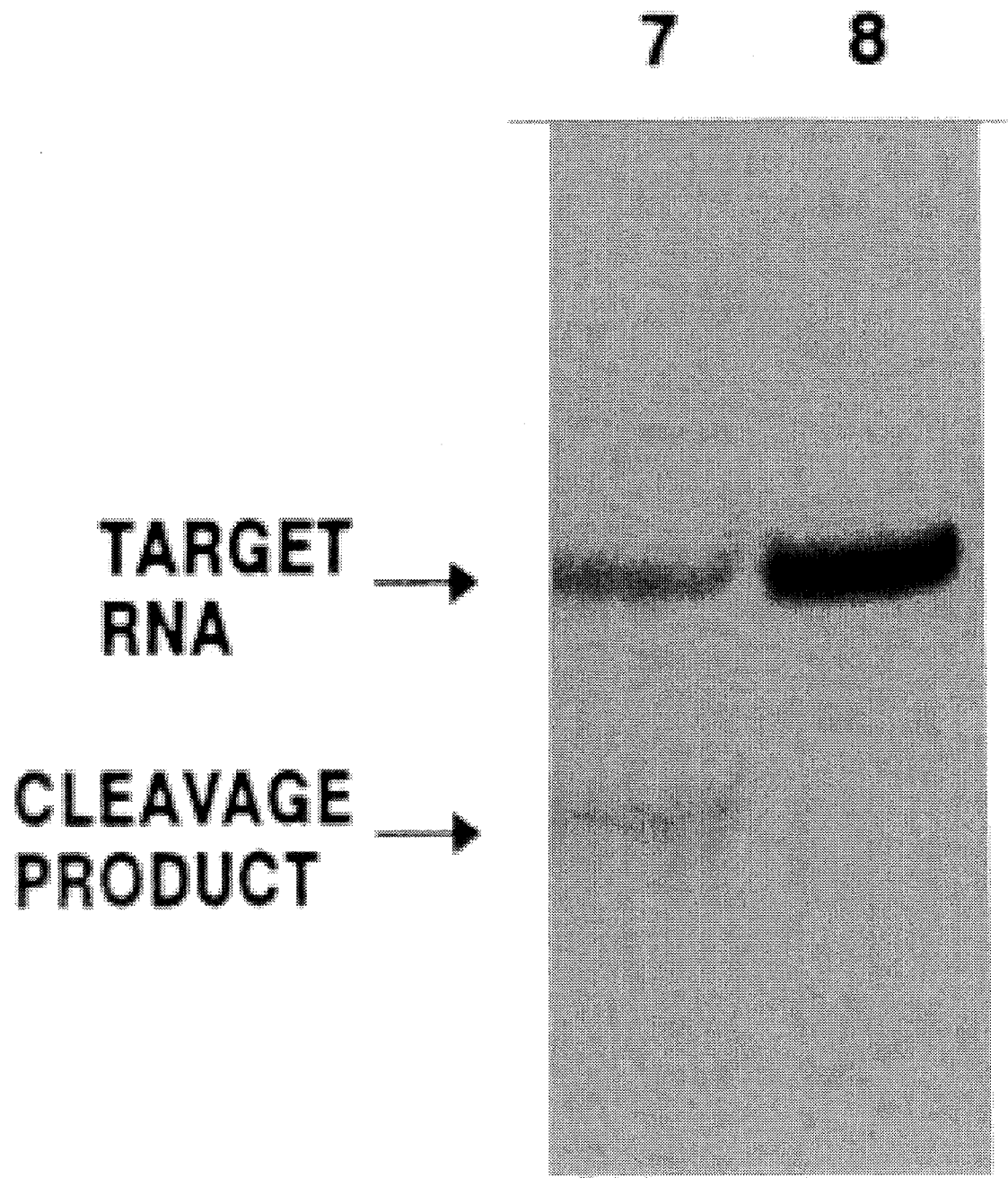

In another experiment, the citrus exocortis viroid (CEV) target site at nucleotide −336 in its complementary RNA was cleaved using a ribozyme (RzCEV2) having the sequence set out in FIG. 14a. The loop region designated with the letter "L" in FIG. 14 comprises six nucleotides having the sequence 3'-CCTATA-5'. This is distinct from the loop region of sTobRV which comprises four nucleotides having the sequence 3'-AGAG-5'. This ribozyme cleaves target CEV complementary RNA at position −336 as shown in the electrophoretic profile of FIG. 14b.

This experiment indicates that the number of nucleotides, and nucleotide sequence of the loop region is unimportant in ribozyme activity. In these experiments, the ribozyme was produced according to methods previously described in the specification.

In another experiment, the effect of base pairing in the catalytic domain (stem region) on ribozyme activity was investigated.

A modified ribozyme corresponding to RzCAT-2 but containing four extra base pairs was prepared and tested. In FIG. 15a, the sequence of the ribozyme Rz CAT-2 is shown hybridized to target CAT RNA. The test ribozyme is shown at 15b, with the additional base pairs boxed. The test ribozyme had comparable activity to that of RzCAT-2. This indicates that the base paired region of the ribozyme catalytic domain may be of variant length, without effecting catalytic activity.

We have observed (data not shown) that the stable in vivo form of sTobRV RNA transcripts expressed in transgenic plants is primarily circular, presumably due to ligation of 5' and 3' termini. Therefore, the use of two autolytic cleavage sites flanking a sequence of interest in an in vivo RNA transcript is likely to lead to a circularized product which may have greater stability than linear transcripts. This approach appears to provide a novel method for in vivo stabilization of ribozyme sequences. This is termed circularization.

EXAMPLE 8

In-vivo Activity of Ribozymes:

The in-vivo activity of ribozymes in plant cells is investigated in this Example.

Experimental Protocol:

Plasmids containing anti-CAT (CAT=chloramphenicol acetyl transferase) or combined anti-CAT/ribozyme gene constructions (see below) were introduced into tobacco protoplasts in the same amount and proportion relative to each other, along with another plasmid which contained a functional CAT gene construction. CAT activities were measured and compared with the base level of gene activity.

Materials and Methods:

(a) Electroporations and CAT assays.

These were performed as described in Llewellyn et al. J. Mol. Biol. (1987) 195:115–123. Briefly, protoplasts of *Nicotiana plumbaginifolia* line T5 were prepared from a suspension two days after subculture, suspended in 10 mM HEPES, pH 7.2, 150 mM NaCl, 0.2M mannitol and adjusted to a density of $3 \times 10^6$/ml. Electroporation was carried out using a single 50 ms pulse at 250 V. Protoplasts were diluted 10-fold and cultured and for 20 hr. at 26° C. in the dark. They were disrupted by sonication and extracts obtained. The extracts were normalized for protein content and assayed for CAT activity in vitro using $^{14}$C-chloramphenicol and acetyl CoA. Reaction products were separated by thin layer chromatography and visualized by autoradiography. Extent of reactions were calculated by the production of radioactive product derivatives from the $^{14}$C-chloramphenicol template.

(b) Gene Constructions.

Gene constructions were introduced into 0.1 ml protoplast suspensions as plasmid DNAs which had been purified from bacteria by extraction and two cycles of CsCl equilibrium density gradient centrifugation. They were resuspended in 10 mM Tris/1 mM EDTA/pH=7.5 for use.

The active CAT gene construction was borne on the plasmid designated pCAT7+. It was derived by fusion of a CAT gene sequence (from plasmid pCM4, see T. J. Close and R. Rodriguez, 1982, Gene 20:305–316) into the plasmid pJ35SN (derived from p35SN, W. L. Gerlach et al., 1987, Nature 328:802–805) so that the active gene construction was:

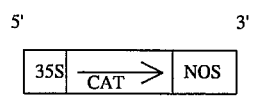

35S refers to the 35S CaMV (cauliflower mosiac virus) promoter, NOS to nopaline synthetase polyadenylation signal, T/C to transcription.

Along with 0.2 ug of pCAT7+ there were added various gene constructions in excess as described below. The gene constructions were contained within plasmids with the following designations:

pJ35SN—This vector plasmid, a map of which is shown in FIG. 16, contains a 35S CaMV promoter and plant nopaline synthase 3' polyadenylation signal, which may be depicted as follows:

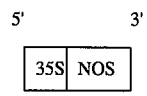

pCAT7—This contains the CAT gene sequence inserted into pJ35SN such that transcription will result in the production of the antisense CAT RNA, which may be depicted as follows:

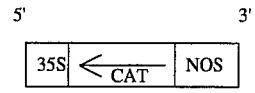

pCAT19—This contains the CAT gene with four catalytic ribozyme domains included within it, (see Example 4 and FIG. 9), inserted into pJ35SN such that transcription will result in the production of antisense CAT RNA containing four catalytic ribozyme domains, which may be depicted as follows:

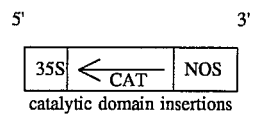
catalytic domain insertions

Results:

The following table shows the relative CAT activities in cells 20 hours after electroporation. Activity is expressed as per cent conversion of chloramphenicol substrate in a 1 hour assay.

| Treatment | ug Plasmid Electroporated | | | | % Conversion |
|---|---|---|---|---|---|
| | pCAT7+ | pJ35SN | pCAT7− | pCAT19− | |
| 1A | | | | | 0 |
| 1B | | | | | 0 |
| 2A | 0.2 | 18 | | | 21 |
| 2B | 0.2 | 18 | | | 46 |
| 3A | 0.2 | 9 | 9 | | 28 |
| 3B | 0.2 | 9 | 9 | | 32 |
| 4A | 0.2 | | 18 | | 26 |
| 4B | 0.2 | | 18 | | 19 |
| 5A | 0.2 | 9 | | 9 | 19 |
| 5B | 0.2 | | | 9 | 22 |
| 6A | 0.2 | | | 18 | 14 |
| 6B | 0.2 | | | 18 | 16 |

(for each treatment "A" and "B" are duplicates)

The following conclusion can be drawn from these results:

(a) The introduction of the CAT gene construction results in significant CAT activity—compare 2A, B with 1A, B. There is variability between duplicates. From the trends seen in the other samples (see "b" and "c" below) it is likely that 2A shows an abnormally low activity.

(b) Concomitant introduction of an antisense gene construction results in a decrease in the level of activity—compare 3A, B and 4A, B with 2B. The extent of the decrease is related directly to the level of the antisense gene added as plasmid—compare 3A, B and 4A, B.

(c) Concomitant introduction of the combined antisense/ribozyme gene construction results in a decrease in gene activity—compare 5A, B and 6A, B with 2B. Furthermore, the decrease is more marked than for the corresponding levels of antisense gene constructions—compare 5A,B with 3A,B, and 6A,B with 4A,B.

The average results for four in-vivo experiments are shown in FIG. 17. In this FIGURE, "control" represents treatment 2. "Antisense" represents treatment 4. "Catalytic" represents treatment 6 and "Background" represents treatment 1.

The catalytic ribozyme inhibits CAT activity an average of 47%, compared to an average of 34% for an antisense ribozyme.

The introduction of ribozyme-bearing genes into plant cells inhibits the activity of genes against which they are targeted. Furthermore, the inhibition is greater than for corresponding antisense RNA molecules.

These results show that ribozymes will be active in animal, plant or microbial cells against a range of target RNA molecules.

The mechanisms of action of the ribozymes in this Example is unclear. For example, the antisense ribozyme may irreversibly hybridize to a target RNA and catalyse phosphodiester bond cleave at one or more selected target sites along the target RNA. Alternatively, cellular enzymes may unwind the antisense RNA from its target sequence, such that the target RNA is cleaved into two or more fragments.

EXAMPLE 9

In-vivo Activity of Ribozymes in Animal Cells:

The activity of ribozymes in inactivating a target RNA in mammalian cells in demonstrated in this Example.

Materials and Methods:

The active gene constructions encoding ribozymes were transfected into the widely available monkey kidney cell line COS1 by electroporation. In this method, $3 \times 10^6$/ml COS1 cells suspended in a buffered saline with 10% FCS (foetal calf serum), were contacted with various gene constructs and an electric discharge applied to effect electroporation of DNA into the cells. The transfected cells were incubated at 37° C. for 48 hours in culture medium before assay for CAT and luciferase activity.

CAT gene constructs were borne on the plasmid designated pTK CAT (Miksicek et al., Cell 46: 283–290, 1986). This plasmid was derived by the introduction of a CAT gene sequence into the plasmid pSV2 such that it is under the control of the thymidine kinase promoter of the herpes simplex virus.

Gene constructs encoding ribozymes were borne on the plasmid pSV232A (De Wet et al., Molecular and Cellular Biology 7: 725–737, 1987) containing the luciferase gene fused to the SV40 early promoter. DNA encoding ribozymes was ligated into the XbaI site at the 3' end of the luciferase gene according to the standard methods of Maniatis et al. (Molecular Cloning, A Laboratory Manual, Cold Spring Harbour, 1982).

The following constructs were prepared using standard techniques of Maniatis et al. (Supra): pFC58—This plasmid vector contains DNA encoding ribozyme RzCAT-1 fused to the 3' end of the luciferase gene in a non-functional orientation.

This may be depicted as follows:

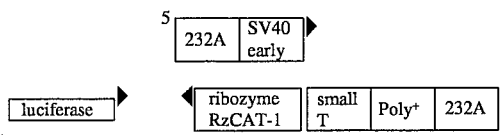

where 232A refers to pSV232A sequences, SV40 early refers to the early promoter of SV40 and small T is DNA encoding the small T intervening sequence of SV40. This construct results in production of an RNA molecule encoding luciferase and the ribozyme RzCAT-1, the latter being in an orientation such that it would not be expected to be catalytic.

pFC4—This plasmid is the same as pFC58 except that RzCAT-1 is replaced with RzCAT-3.

pFC1-6—This plasmid is the same as pFC58 except that RzCAT-1 is replaced with RzCAT-3 in the sense orientation (5'-3').

pFC20—This plasmid is the same as pFC1-6 except that RzCAT-3 is replaced with RzCAT-2 having eight nucleotide flanking sequences.

pFC12—This plasmid is the same as pFC20 except that the ribozyme RzCAT-2 contains twelve nucleotide flanking sequences.

pFC50—This plasmid contains the CAT gene with four catalytic ribozyme domains included within it (see Example 4 and FIG. 9) in the sense orientation (5'-3'), which on transcription gives rise to an inactive ribozyme. This plasmid may be depicted as follows:

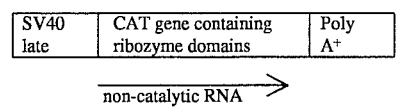

pFC54—This plasmid is the same as pFC50, except that the CAT gene and the ribozyme domains are in the antisense (3'-5') active orientation.

pFC64—This plasmid shares the SV40 promoter and polyadenylation signals with pFC50 and contains the wild type CAT gene with no inserted ribozyme domains. This gene is in an antisense orientation, and thus does not produce CAT protein.

pFC65—This plasmid is the same as pFC64 except that the wild type CAT gene is in the sense (5'-3') orientation and is thus productive of CAT protein.

Assays:

Luciferase activity was assayed according to the methods of De Wet et al. (Supra). Briefly, COS cells were lysed 48 hours after transfection, and the cell lysate incubated with luciferin, the substrate of luciferase, and luminesence detected using a scintillation counter.

CAT activity was also measured using COS cell lysates (cell lysates were divided into two, and each portion assayed either for luciferase or CAT activity), according to the method of Sleigh, M.J., Anal. Biochem. 156: 251–256, (1986).

In the in-vivo assays, pFC58 and pFC4 did not effect CAT activity in transfected cells. This activity was designated 100% CAT activity and 0% CAT suppression. CAT activity in cells transfected with other plasmids was measured relative to pFC58. The % of CAT suppression was measured as $$100 - \left( \frac{CAT_{test}}{CAT_{control}} \right) \times 100$$

normalised to luciferase production. $CAT_{test}$=CAT assay result for test constructs. CAT control=CAT assay for control constructs (pFC4 and pFC58).

Luciferase production is an internal control for electroporation, and gives a measure of ribozyme production within each individually electroporated tissue culture plate.

Results:

| | Experiment (i) | | | | |
|---|---|---|---|---|---|
| Treatment | μg plasmid electroporated/$1.5 \times 10^6$ cells | | | | % CAT Suppression |
| | pTKCAT | pFC58 | pFC20 | pFC1-6 | pFC12 | |
| 1 | 5 | | 2 | | | 56 |
| 2 | 5 | | 1 | 1 | | 53 |
| 3 | 5 | | | | 2 | 40 |
| 4 | 5 | 2 | | | | 0 |

All treatments were carried out in duplicate and an average value given.

Experiment (ii)

| Treatment | μg plasmid electroporated/1.5 × 10⁶ cells | | | | | % CAT Suppression |
|---|---|---|---|---|---|---|
| | pTKCAT | pFC-1-6 | pFC20 | pFC12 | pFC4 | |
| 5 | 5 | 2 | | | | 75 |
| 6 | 5 | | 2 | | | 75 |
| 7 | 5 | | 4 | | | 62 |
| 8 | 5 | 1 | 1 | | | 70 |
| 9 | 5 | | | 4 | | 51 |
| 10 | 5 | | | | 2 | 0 |

Treatments 5 to 10 were carried out in duplicate and an average value given.

Experiment (iii)

| Treatment | μg plasmid electroporated/ 1.5 × 10⁶ cells | | | % CAT Suppression |
|---|---|---|---|---|
| | pTKCAT | pFC1-6 | pFC4 | |
| 11 | 5 | 2 | | 66 |
| 12 | 5 | | 2 | 0 |

Treatments were carried out in quintuplicate and an average value given.

Experiment (iv)

| Treatment | μg plasmid electrophorated | | | | | % CAT Suppression |
|---|---|---|---|---|---|---|
| | pTKCAT | pFC50 | pFC54 | pFC64 | pFC65 | |
| 13 | 5 | 2 | | | | 0 |
| 14 | 5 | | 2 | | | 26 |
| 15 | 5 | | | 2 | | 2 |
| 16 | 0 | | | | 2 | NA |

Each of treatments 13 to 16 were carried out in quadruplicate.
The sense CAT construction (treatment 16) was productive of high levels of CAT activity in its own right. Therefore % suppression is not applicant (NA).

A number of experiments were also conducted with the TK promoter of pTKCAT replaced with the human metallothionein promoter. When this CAT construct was co-transfected into COS1 cells with plasmids encoding one or more ribozymes, a marked decrease in CAT activity was observed.

The above results clearly demonstrate the in-vivo inactivating activity of ribozymes in animal cells.

Whilst the effectiveness of the ribozymes in vivo, is believed to be caused by one or more catalytic regions which are capable of cleavage of a target RNA, the presence of such regions in "Antisense" RNA type ribozymes may not actually lead to cleavage in vivo if the entire RNA/antisense RNA molecule does not fall apart. However, regardless of whether the molecule falls apart or not, the foregoing Examples demonstrate the effectiveness of the ribozyme in inactivating the target RNA. Thus, the invention is applicable to all ribozymes having a catalytic region capable of causing cleavage and a hybridizing region, regardless as to whether cleavage actually occurs in the target RNA. i.e. The hybridizing region may be so large as to cause the combined RNA/ribozyme to stay together and prevent the target RNA being cleaved into separated components even though the catalytic region is itself capable of causing cleavage.

We claim:

1. A compound having the formula:

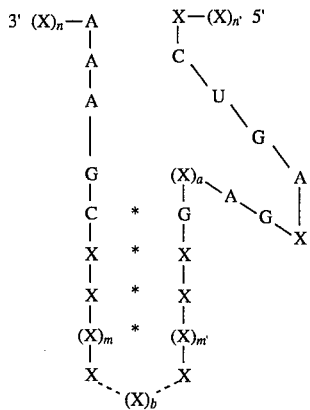

wherein each X represents a ribonucleotide which may be the same or different;

wherein each of $(X)_n$ and $(X)_{n'}$ represents an oligoribonucleotide having a predetermined sequence which is (a) capable of hybridizing with an RNA target sequence to be cleaved and (b) does not naturally occur covalently bound to the sequences A—A—A—G—C— and X—C—U—G—A—, respectively, such RNA target sequence not being present within the compound;

wherein each of n and n' represents an integer which defines the number of ribonucleotides in the oligonucleotide with the proviso that the sum of n +n' is greater than or equal to 14;

wherein each * represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the G located 3' of $(X)_a$;

wherein each of m and m' represents an integer which is greater than or equal to 1;

wherein each of the dashed lines independently represents either a chemical linkage providing covalent bonds between the ribonucleotides located on either side thereof or the absence of any such chemical linkage; and wherein $(X)_b$ represents an oligoribonucleotide which may be present or absent with the proviso that b represents an integer which is greater than or equal to 2 if $(X)_b$ is present.

2. A compound of claim 1, wherein each of n and n' is greater than or equal to 6.

3. A transfer vector comprised of RNA or DNA or a combination thereof containing a nucleotide sequence which on transcription gives rise to a compound of any of claims 1 and 2.

4. A transfer vector according to claim 3 which is a bacterial plasmid or phage DNA.

5. A method of using the transfer vector of claim 3 to produce the compound in a host cell which comprises: introducing the transfer vector into a suitable host cell and culturing the host cell under conditions to express the transfer vector so as to thereby produce the compound in the host cell.

6. A method of using the transfer vector of claim 3 which comprises introducing a suitable vector into a suitable eukaryotic host cell and culturing the host cell so as to effect transcription of the nucleotide sequence contained within the transfer vector and thereby produce the compound encoded by such nucleotide sequence, which compound is capable of hybridizing with and specifically cleaving an RNA target sequences within the eukaryotic host cell.

* * * * *